(12) United States Patent
Wortzman et al.

(10) Patent No.: US 8,455,459 B2
(45) Date of Patent: Jun. 4, 2013

(54) METHOD OF APPLYING AN INJECTABLE FILLER

(75) Inventors: Mitchell S. Wortzman, Scottsdale, AZ (US); Rhoda Narins, Scarsdale, NY (US); Xiaoming Lin, Cave Creek, AZ (US)

(73) Assignee: Medicis Pharmaceutical Corporation, Irvine, CA (US)

( * ) Notice: Subject to any disclaimer, the term of this patent is extended or adjusted under 35 U.S.C. 154(b) by 893 days.

(21) Appl. No.: 12/184,966

(22) Filed: Aug. 1, 2008

(65) Prior Publication Data

US 2009/0035251 A1 Feb. 5, 2009

Related U.S. Application Data

(60) Provisional application No. 60/953,661, filed on Aug. 2, 2007.

(51) Int. Cl.
| | | |
|---|---|---|
| *A61K 31/715* | (2006.01) | |
| *A61K 9/00* | (2006.01) | |
| *A61K 9/14* | (2006.01) | |
| *A61F 13/00* | (2006.01) | |
| *C07H 3/00* | (2006.01) | |

(52) U.S. Cl.
USPC ............. 514/54; 424/400; 424/422; 424/488; 536/123.1

(58) Field of Classification Search
USPC ........... 514/54; 424/400, 422, 488; 536/123.1
See application file for complete search history.

(56) References Cited

U.S. PATENT DOCUMENTS

| | | |
|---|---|---|
| 3,768,472 A | 10/1973 | Hodosh et al. |
| 5,007,040 A | 4/1991 | Okauchi |
| 5,026,357 A | 6/1991 | Przuntek et al. |
| 5,128,326 A | 7/1992 | Balazs et al. |
| 5,143,724 A | 9/1992 | Leshchiner et al. |
| 5,275,095 A | 1/1994 | Van Haren |
| 5,399,351 A | 3/1995 | Leshchiner et al. |
| 5,633,001 A | 5/1997 | Agerup |
| 5,827,937 A | 10/1998 | Agerup |
| 6,159,161 A | 12/2000 | Hodosh |
| 6,371,939 B2 | 4/2002 | Bergens et al. |
| 7,192,984 B2 | 3/2007 | Berg et al. |
| 2004/0050006 A1 | 3/2004 | Park et al. |
| 2004/0101959 A1 | 5/2004 | Marko et al. |
| 2004/0225276 A1 | 11/2004 | Burgess et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2006/0035861 A1 | 2/2006 | Berg et al. |
| 2006/0073178 A1 | 4/2006 | Giampapa et al. |
| 2006/0182725 A1 | 8/2006 | Marko et al. |
| 2007/0071729 A1 | 3/2007 | Bernstein |
| 2007/0102010 A1* | 5/2007 | Lemperle et al. ............. 128/898 |
| 2007/0154416 A1 | 7/2007 | Hattendorf et al. |
| 2007/0154421 A1 | 7/2007 | Hattendorf et al. |
| 2007/0154493 A1 | 7/2007 | Hattendorf et al. |
| 2007/0178121 A1 | 8/2007 | First et al. |
| 2008/0003241 A1 | 1/2008 | Marx et al. |
| 2008/0038306 A1 | 2/2008 | David |
| 2008/0107744 A1 | 5/2008 | Chu |
| 2009/0204101 A1 | 8/2009 | Wortzman et al. |

FOREIGN PATENT DOCUMENTS

| | | |
|---|---|---|
| WO | WO 87/07898 | 12/1987 |
| WO | WO 98/40027 | 9/1998 |
| WO | WO 99/11196 | 3/1999 |
| WO | WO 00/35375 A1 | 6/2000 |
| WO | WO 02/36902 A1 | 5/2002 |
| WO | WO 03/007782 A2 | 1/2003 |
| WO | WO 2004/048557 A1 | 6/2004 |
| WO | WO 2005/051316 A2 | 6/2005 |
| WO | WO 2005/051444 A2 | 6/2005 |
| WO | WO 2005/051452 A2 | 6/2005 |
| WO | WO 2005/120597 A1 | 12/2005 |
| WO | WO 2006/052451 A2 | 5/2006 |
| WO | WO 2006/065800 A2 | 6/2006 |
| WO | WO 2006/102676 A1 | 9/2006 |
| WO | WO 2006/116210 A2 | 11/2006 |
| WO | WO 2006/116210 A3 | 11/2006 |
| WO | WO 2006/127467 A2 | 11/2006 |
| WO | WO 2007/041677 A2 | 4/2007 |
| WO | WO 2007/070561 A2 | 6/2007 |
| WO | WO 2007/089454 A2 | 8/2007 |
| WO | WO 2007/106457 A2 | 9/2007 |
| WO | WO 2007/106457 A3 | 9/2007 |
| WO | WO 2008/031525 A1 | 3/2008 |
| WO | WO 2008/070893 A1 | 6/2008 |
| WO | WO 2008/072229 A2 | 6/2008 |
| WO | WO 2008/086560 A1 | 7/2008 |

OTHER PUBLICATIONS

Kanchwala et al., Annals of Plastic Surgery, 2005, 55(1), 30-35.*
"Patient Consent for Treatment With Medicis Aesthetics Product: Restylane®" downloaded from heddenmd.com/pdf/restylane/pdf on Oct. 2, 2008. Earliest publication unknown. First online capture by http://relay.waybackmachine.org is Feb. 20, 2004, © 2004 and Oct. 9, 2004, © 2004.
"Procedures—Restylane", Midwest Dermatologic Laser and Vein Centre. © 2006 Downloaded from http://drkovaklaser.com/laser-hair-removal-chicago/procedures/restylane_chicago.htm on Oct. 2, 2008. Earliest publication unknown. First online capture by http://replay.waybackmachine.org is Mar. 22, 2004, © 2003 and Dec. 10, 2006, © 2006.

(Continued)

*Primary Examiner* — Abigail Fisher
(74) *Attorney, Agent, or Firm* — Len Smith; Eli A. Loots; Madhavi S. Patankar

(57) ABSTRACT

Methods for applying injectable fillers are provided. In some embodiments, the methods can extend effectiveness of the injectable filler. In some embodiments, the methods can provide for an elevated level of effectiveness of the injectable filler. In some embodiments, the methods can prolong the effectiveness of the injectable filler.

46 Claims, 11 Drawing Sheets

OTHER PUBLICATIONS

American Association for Aesthetic Plastic Surgery. Cosmetic Surgery National Data Bank: 2006 Statistics. http://www.surgery.org/download/2006stats.pdf. Accessed Aug. 2, 2007.

Carruthers et al. Randomized, double-blind comparison of the efficacy of two hyaluronic acid derivatives, Restylane®, Perlane®, and Hylaform®, in the treatment of nasolabial folds. Dermatol Surg 2005; 31 (11 pt 2): 1591-1598.

Carruthers et al., "Cosmetic Uses of Botulinum A Exotoxin." In: Klein A, editor. Tissue Augmentation in Clinical Practice: Procedures and Techniques. New York: Marcel Dekker; (1998): Chpt 11, pp. 207-236.

Day et al. The Wrinkle Severity Rating Scale: a validation study. Am J Clin Dermatol 2004, 5: 49-52.

DeLorenzi et al. Multicenter Study of the efficacy and safety of subcutaneous non-animal-stabilized hyaluronic acid in aesthetic facial contouring: interim report. Dermatol. Surg 2006; 32: 205-211.

Duranti et al. Injectable hyaluronic acid gel for soft tissue augmentation: A clinical and histological study. Dermatol Surg 1998, 24: 1317-1325.

Gormley et al. "Quantitative assessment of augmentation therapy" J Dermatol Surg Oncol, 1990, 16(12) 1147-1151.

International Search Report and Written Opinion received in International Application No. PCT/US08/72016, dated Oct. 24, 2008.

International Preliminary Report on Patentability received in International Application No. PCT/US08/72016, dated Feb. 11, 2010.

Lowe et al. Adverse Reactions to Dermal Fillers: Review. Dermatol Surg 31:11 Part 2:Nov. 2005. p. 1616-1625.

Machin et al. Sample size tables for clinical studies. $2^{nd}$ Edition, Blackwell Science Ltd., Oxford, England, (1997): Chpt 5, pp. 99-130.

Medicis Announces FDA Approval of PMA Supplement for Restylane®, Press Release, Oct. 10, 2008, Medicis Pharmaceuticals Inc. 2 pages.

Miller, Scott R. "Injectable Fillers Overview" Consumer Guide to Plastic Surgery, updated Jun. 2008, © 2005, Ceatus Media Group LLC, accessed at http://www.yourplasticsurgeryguide.com/injectables-and-fillers/injectable-fillers.htnn on Oct. 1, 2008. Earliest publication unknown. First online capture by http://replay.waybackmachine.org is Jul. 17, 2006, © 2005.

Narins et al. "A Randomized, Double-Blind, Multicenter Comparison of the Efficacy and Tolerability of Restylane Versus Zyplast for the Correction of Nasolabial Folds." Dermatologic Surgery, 2003, 29 (6):588-595.

Narins et al. "Persistence and Improvement of Nasolabial Fold Correction with Nonanimal-Stabilized Hyaluronic Acid 100,000 Gel Particles/mL Filler on Two Retreatment Schedules: Results up to 18 Months on Two Retreatment Schedules" Dermatologic Surgery, Jun. 2008, 34 (S1): S2-S8.

Olenius, M. The first clinical study using a new biodegradable implant for the treatment of lips, wrinkles, and folds. Aesth Plast Surg 1998, 22: 97-101.

Perlane® Package Insert, printer-friendly version. Revised Feb. 2009. Downloaded from http://www.medicis.com/products/pi/pi_perlane_printer.pdf on Jul. 19, 2010.

Rao et al. Clinical comparison between two hyaluronic-acid derived fillers in the treatment of nasolabial folds: Hylaform® versus Restylane®. Dermatol Surg 2005; 31: 1587-90.

Restylane® Package Insert, printer-friendly version. Revised Dec. 2008. Downloaded from http://www.medicis.com/products/pi/pi_restylane_printer.pdf on Jul. 19, 2010.

Rundle, Rhonda. Wrinkle Drug's Action is Found. The Wall Street Journal, Feb. 20, 2007.

Siegel, Michel. "Restylane® Treatment in Houston", Facial Center for Plastic Surgery, printed from website http://www.houstonfaces.com/houston-restylane-treatments.asp, on Oct. 2, 2008. Earliest publication unknown. First online capture by http://replay.waybackmachine.org is Aug. 22, 2007.

Wang et al. "In Vivo Stimulation of De Novo Collagen Production Caused by Cross-linked Hyaluronic Acid Dermal Filler Injections in Photodamaged Human Skin", Arch Dermatol 2007, 143: 155-163.

Restylane® Instructions for Use Aug. 2009.

Restylane Fine Lines™ Instructions for Use Mar. 2005.

Man et al. "A Double-Blind, Comparative Study of Nonanimal-Stabilized Hyaluronic Acid versus Human Collagen for Tissue Augmentation of the Dorsal Hands." Dermatologic Surgery 34.8 (Aug. 2008) 1026-1031.

Matarasso et al. "Consensus Recommendations for Soft-Tissue Augmentation with Nonanimal Stabilized Hyaluronic Acid (Restylane)" Plastic and Reconstructive Surgery 117 (Mar. 2006) 3S-34S.

Monheit, GD. Hylaform: a new hyaluronic acid filler. Facial Plast Surg 2004; 20:153-5.

Monheit, GD. Hyaluronic acid fillers: Hylaform and Captique. Facial Plast Surg Clin North Am 2007; 15:77-84.

"New study shows that the effect of treatment with Restylane® lasts for up to 18 months with one repeat treatment." Oct. 2008. Downloaded from www.tinkable.co.uk/pdf/restylane.pdf.

Perlane® package insert, downloaded Aug. 1, 2008 from Medicis website. Publicly available prior to Aug. 1, 2008.

Perlane® prescribing information. Scottsdale (AZ): Medicis Aesthetics Inc.

Perlane® package insert. Revised Aug. 2010.

Perlane® package insert. First made public: May 2007.

Perlane® package insert. First made public: Feb. 10, 2009.

Perlane® package insert. First made public: Nov. 4, 2010.

Perlane-L™ Injectable Gel with 0.3% Lidocaine package insert. Revised May 2010.

Perlane-L™ Injectable Gel with 0.3% Lidocaine package insert. First made public: Feb. 1, 2010.

Perlane-L™ Injectable Gel with 0.3% Lidocaine package insert. First made public: May 2010.

Restylane® package insert. Revised Aug. 2010.

Restylane® package insert. First made public: 2003.

Restylane® package insert. First made public: 2004.

Restylane® package insert. First made public: Jan. 2005.

Restylane® package insert. First made public: Dec. 5, 2005.

Restylane® package insert. First made public: Jun. 4, 2008.

Restylane® package insert. First made public: Oct. 16, 2008.

Restylane® package insert. First made public: Dec. 11, 2008.

Restylane® package insert. First made public: Oct. 22, 2010.

Restylane-L™ Injectable Gel with 0.3% Lldocaine package insert. Revised May 2010.

Restylane-L™ Injectable Gel with 0.3% Lldocaine package insert. First made public: Feb. 1, 2010.

Restylane-L™ Injectable Gel with 0.3% Lldocaine package insert. First made public: May 18, 2010.

Radiesse® Injectable Implant, Instructions for Use, 14 pages.

Restylane® Injectable Gel package insert, downloaded Aug. 1, 2008 from Medicis website. Publicly available prior to Aug. 1, 2008.

Restylane® prescribing information. Scottsdale (AZ): Medicis Aesthetics Inc.

Rubin et al. "Hyaluronic Acid Gel (Restylane®) Implantation Longevity over 52 Weeks." Oct. 28, 2007, Abstract only.

Shamban, Ava T. "Combination Hand Rejuvenation Procedures." Aesthetic Surgery Journal 29.5 (Sep. /Oct. 2009) 409-413.

Strobos, Jur. "Study Protocol—A Randomized, Comparative, Evaluator-Blinded Study of the Safety and Efficacy of Restylane® and Perlane® in Patients with Fitzpatrick Skin Types 4, 5 or 6." Jun. 2005.

Strobos, Jur. "Postapproval Clinical Study Report—A Randomized, Comparative, Evaluator-Blinded Study of the Safety and Efficacy of Restylane® and Perlane® in Patients with Fitzpatrick Skin Types 4, 5, or 6." May 2006.

Williams et al. "Changes in skin physiology and clinical appearance after microdroplet placement of hyaluronic acid in aging hands." Journal of Cosmetic Dermatology 8 (2009) 216-225.

Brandt et al., "Hyaluronic acid gel fillers in the management of facial aging," Clinical Interventions in Aging, 2008, pp. 153-159, vol. 3, No. 1.

Chan, H., "Effects of injection duration on site-pain intensity and bruising associated with subcultaneous heparin," Journal of Advanced Nursing, Sep. 2001, pp. 882-892, vol. 35, Issue 6.

Dr. Kane's Declaration 1.132, 2011.

Kablik et al., "Comparative physical properties of hyaluronic acid dermal fillers," Dermatol. Surg., Feb. 2009, pp. 302-312, vol. 35, No. 51.

Office Action dated Dec. 18, 2012, received in U.S. Appl. No. 12/194,934.
A Patient's Guide Radiesse® for the Restoration and/or Correction of the Signs of Facial Loss in People with Human Immunodeficiency Virus, Nov. 2006, 7 pages. Radiesse® Injectable Implant; Instructions for Use, 12 pages.
File History, U.S. Appl. No. 12/194,934, filed Aug. 20, 2008.
Perlane® prescribing information. Scottsdale (AZ): Medicis Aesthetics Inc. Revised Feb. 2009.
Restylane® prescribing information. Scottsdale (AZ): Medicis Aesthetics Inc. Revised Dec. 2008.
André P., Evaluation of the safety of a non-animal stabilized hyaluronic acid (NASHA, Q-Medical, Sweden) in European countries: a retrospective study from 1997 to 2001. J Eur Acad Dermatol Venereol 2004; 18:422-5.
Baer et al. "Effectiveness of a Jet Injection System in Administering Morphine and Heparin to Healthy Adults." *American Journal of Critical Care* 5.1 (Jan. 1996) 42-48.
CTA Injectable HA Gel label, 8 pages, © 2006.
Day et al. "The Wrinkle Severity Rating Scale: A Validation Study." *American Journal of Clinical Dermatology* 5.1 (2004) 49-52.
Dover et al. "Assessment of Acute Safety at 2 Weeks in Subjects Injected Implanted with Hyaluronic Acid Gel Dermal Fillers." Oct. 28, 2007, Abstract only.
Friedman PM et al., Safety data of injectable nonanimal stabilized hyaluronic acid gel for soft tissue augmentation. Dermatol Surg 2002; 28:491-4.
Gillette et al. "New Fillers Finding Favor in Facial Esthetic Enhancement." *Dermatology Times* (Sep. 1, 2005) 1-3.
Glogau and Kane, "Effect of Injection Techniques on the Rate of Local Adverse Events in Patients Implanted with Nonanimal Hyaluronic Acid Gel Dermal Fillers", Dermatol Surg 2008, 34:S105-S109.
Glogau, "Assessment of the Effect of Injection Techniques on the Rate of Local Adverse Events Using Hyaluronic Acid Gel Dermal Fillers" ASPS Oct. 25, 2007.
Hamilton RG et al., Immunogenicity studies of cosmetically administered non-animal stabilized hyaluronic acid particles (accepted for publication), (http://www.ncbi.nlm.nih.gov/pubmed/18086056?ordinalpos=3&itool=EntrezSystem2.PEntrez.Pubmed.Pubmed_ResultsPanel.Pubmed_RVDocSum) Dermatol Sure 2007;33:S176-85.
Hartmann et al. "Hand augmentation with stabilized hyaluronic acid (Macrolane™ VRF20 and Restylane® Vital, Restylane® Vital Light)." *Journal of the German Society of Dermatology* 8 (Jan. 2010) 41-44.
Hylaform® (hylan B gel) label, 8 pages, © 2004.
"Introducing Restylane® SUBQ: Greater Definition for the Cheeks and Chin" Brochure, 6 pages, (c) 2006.
Juvederm® 30 Injectable gel label, 11 pages, © 2006.
Klein, Arnold W., ed. Tissue Augmentation in Clinical Practice: Procedures and Techniques. New York: Marcel Dekker (1998): pp. 1-62, 97-177, 191-205, 237-306, and 379-385.
Lacarrubba et al. "Mesotherapy for skin rejuvenation: assessment of the subepidermallow-echogenic band by ultrasound evaluation with cross-sectional B-mode scanning." *Dermatologic Therapy* 21 (2008) S1-S5.
Levenberg et al. "Clinical results of skin remodeling using a novel pheumatic technology." *International Journal of Dermatology* 49 (Dec. 2010) 1432-1439.
Lindqvist C. et al., A randomized, evaluator-blind, multicenter comparison of the efficacy and tolerability of Perlane versus Zyplast in the correction of nasolabial folds. Plast Reconstr Surg 2005; 115:282-9.
Lowe NJ et al., "Adverse Reactions to Dermal Fillers: Review." *Dermatology Surgery* 31 (Nov. 2005) 1616-1625.
Lowe NJ et al., Hyaluronic acid skin fillers: adverse reactions and skin testing. J Am Acad Dermatol 2001; 45:930-3.

* cited by examiner

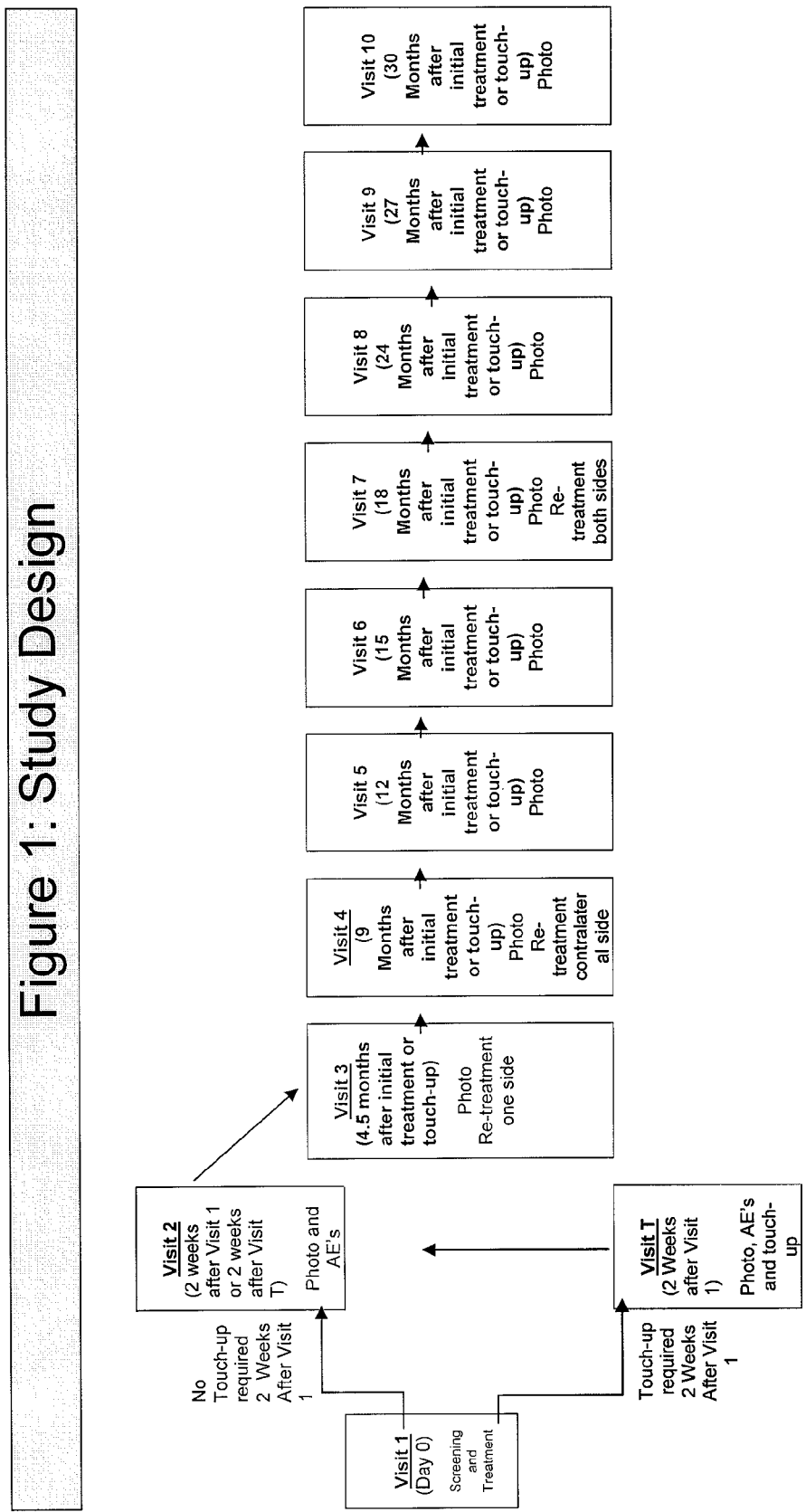

FIGURE 2: SCHEDULE OF STUDY EVALUATIONS

| | Screening and Treatment | Optional Touch-up | 2 Week Follow-Up | 4.5 month Follow-Up | 9 month Follow-Up | 12 month Follow-Up | 15 month Follow-Up | 18 month Follow-Up | 24 month Follow-Up | 27 month Follow-Up | 30 month Follow-Up |
|---|---|---|---|---|---|---|---|---|---|---|---|
| | Visit 1 | Visit T | Visit 2 | Visit 3 | Visit 4 | Visit 5 | Visit 6 | Visit 7 | Visit 8 | Visit 9 | Visit 10 |
| | Day 0 | 2 weeks after initial treatment (± 1 week) | 2 weeks after initial treatment or touch-up (± 1 week) | 4.5 months after initial treatment or touch-up (± 1 week) | 9 months after initial treatment or touch-up (± 1 week) | 12 months after initial treatment or touch-up (± 1 week) | 15 months after initial treatment or touch-up (± 1 week) | 18 months after initial treatment or touch-up (± 1 week) | 24 months after initial treatment or touch-up (± 1 week) | 27 months after initial treatment or touch-up (± 1 week) | 30 months after initial treatment or touch-up (± 1 week) |
| Procedure | | | | | | | | | | | |
| Assessment of Eligibility | X | | | | | | | | | | |
| Medical History | X | | | | | | | | | | |
| Physical Examination | X | | | | | | | | | | |
| Randomization | X | | | | | | | | | | |
| Administration of Implant | X | X[a] | | X[b] | X[b] | | | X[a] | | | |
| Severity Rating Scale | X | X | X | X | X | X | X | X | X | X | X |
| Aesthetic Improvement | | X | X | X | X | X | X | X | X | X | X |
| Concomitant Meds/Procedures | X | X | X | X | X | X | X | X | X | X | X |
| Assessment of AEs | X | X | X | X | X | X | X | X | X | X | X |
| Archival Photographs[c] | X | X | X | X | X | X | X | X | X | X | X | a Both nasolabial folds treated to optimal correction
b One nasolabial fold treated to optimal correction, according to the randomization schedule
c The photographs can be obtained in accordance with the standard practice of the study facility and each set of photographs can include at least one direct frontal view centered on the study participant's face (both nasolabial folds should be clearly visible)

[1] The positive change from initial baseline visit (current visit WSRS - initial visit WSRS).

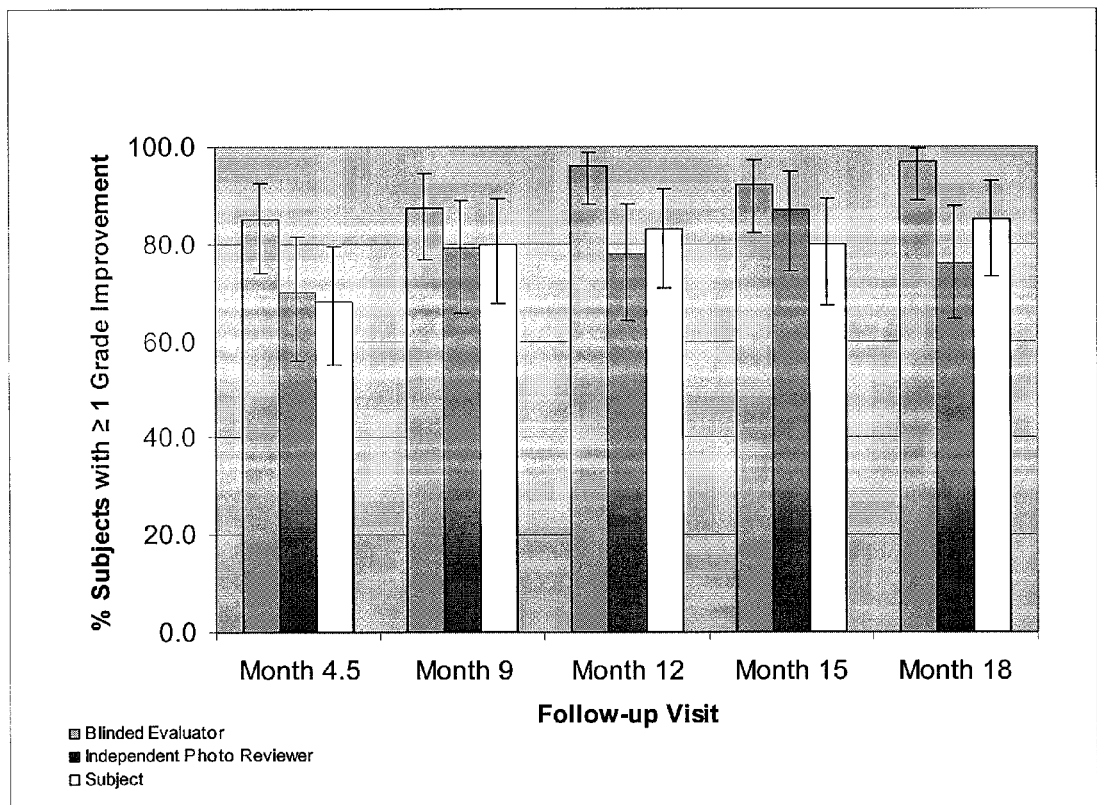
FIG. 8: Proportion of subjects with at least one grade improvement from baseline – side re-treated at 4.5 months

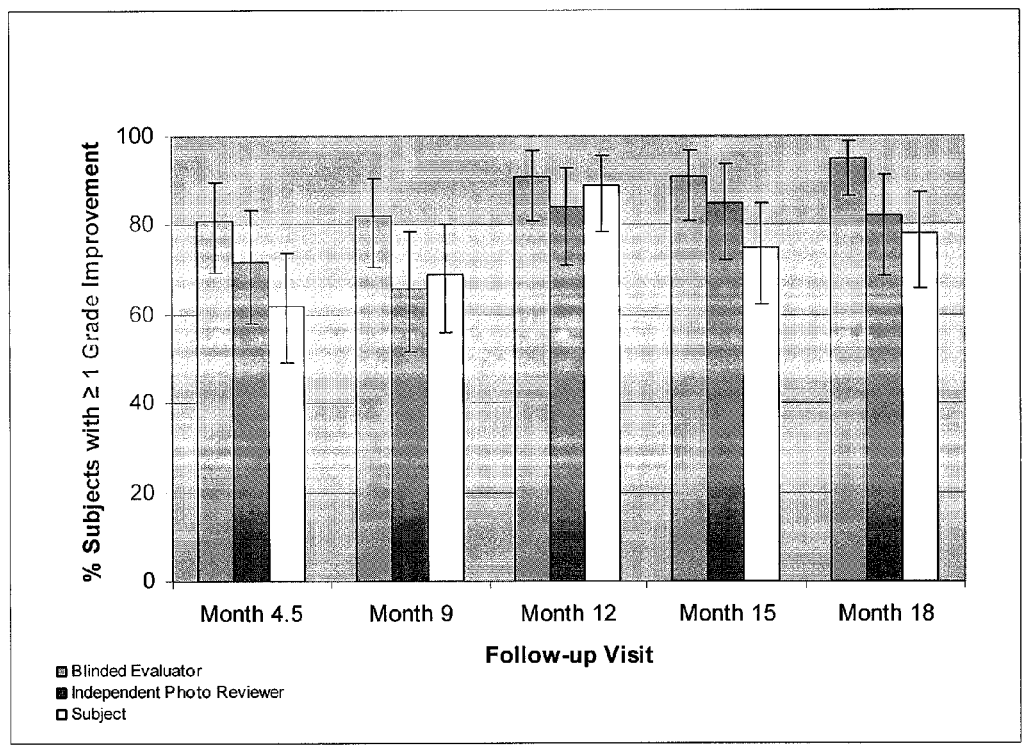
Error bar=Exact 95% confidence interval of the proportion
FIG. 9: Proportion of subjects with at least one grade improvement from baseline – side re-treated at 9 months

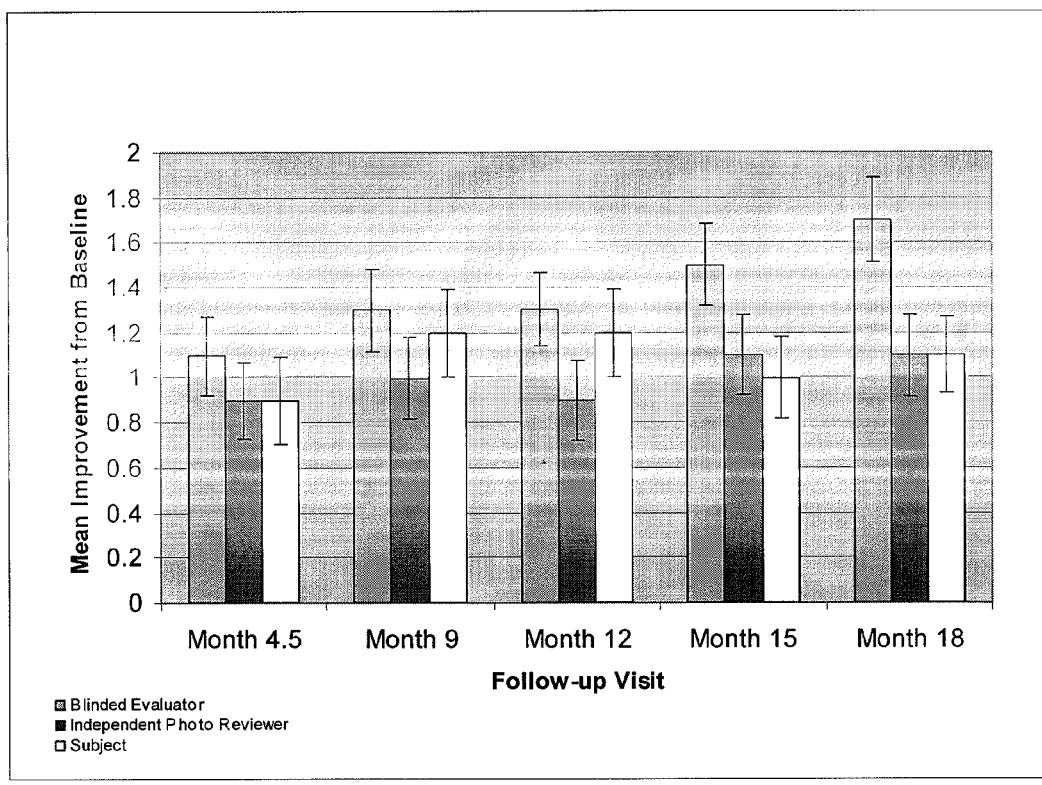
FIG. 10: Mean improvement from baseline – side re-treated at 4.5 months

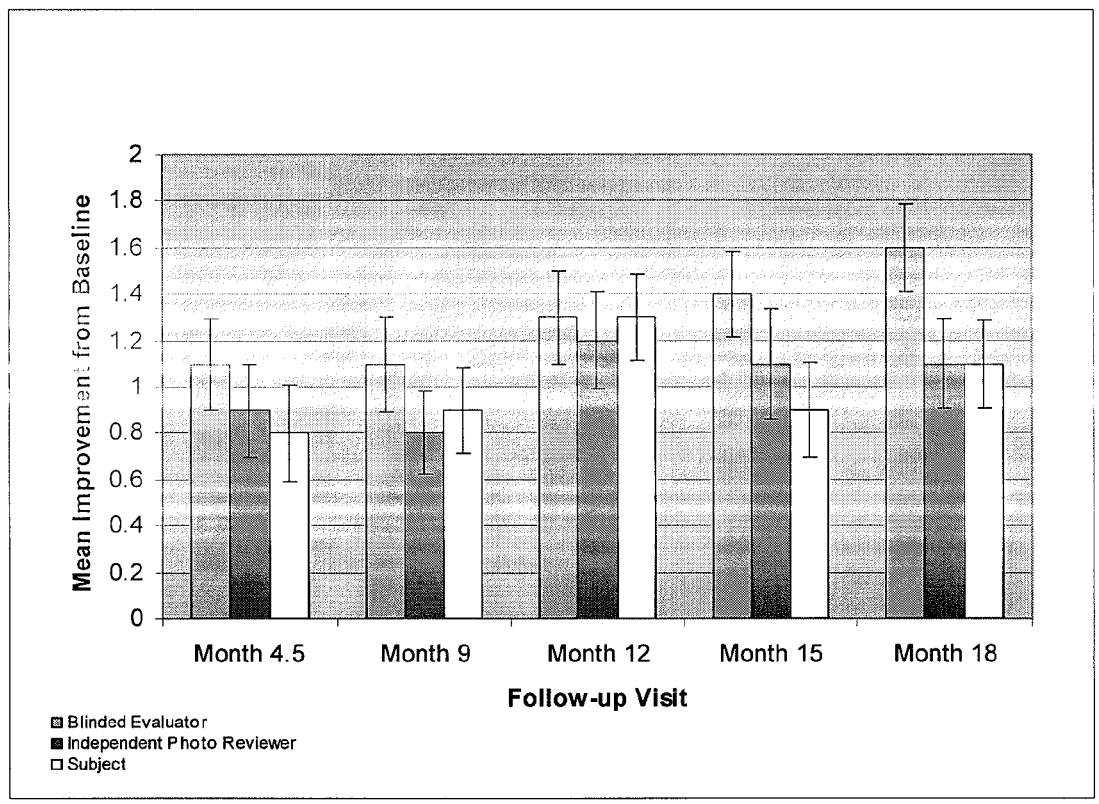
FIG. 11: Mean improvement from baseline – side re-treated at 9 months

METHOD OF APPLYING AN INJECTABLE FILLER

RELATED APPLICATIONS

This application claims priority to U.S. Provisional Application Ser. No. 60/953,661, filed Aug. 2, 2007, hereby incorporated by reference in its entirety.

FIELD OF THE INVENTION

Methods and systems for using dermal fillers are disclosed.

BACKGROUND OF THE INVENTION

Description of the Related Art

A variety of methods and substances exist for adding volume or firmness to a subject or subject's face for cosmetic purposes. Despite the fact that such methods are being used with ever increasing frequency, the art has seen little in the way of developments in regard to certain aspects of these treatment methods.

SUMMARY OF THE INVENTION

In some aspects, the present disclosure provides a method for maintaining and/or prolonging injectable filler composition efficacy. This can be especially relevant to increase the aesthetic benefit of implanted materials.

In some aspects, the present disclosure provides a method of injecting an injectable filler such as hyaluronic acid (HA) so that it provides longer lasting, superior, or longer lasting and superior benefits. In some embodiments, these benefits can include improved volume and/or firmness to a subject's skin.

In some aspects, the invention comprises a method for providing an injectable filler composition to a subject for cosmetic purposes. The method can comprise performing an initial treatment session on a subject that comprises a first injection of a first injectable filler composition into the subject at a target area, thereby providing an increase in volume and/or firmness to the target area. The method can further comprise performing a re-treatment session on the subject. The re-treatment session can comprise a second injection of a second injectable filler composition into the target area at a time subsequent to the initial treatment session. The second injection extends the increase in volume and/or firmness of the target area. The time subsequent to the initial treatment session is in the range of 1 month to less than 9 months, and at least one of the first or second injectable filler compositions comprises hyaluronic acid.

In some aspects, the invention comprises a method for providing a target area of a subject with a continuing increase in firmness and/or volume following a re-treatment session of an injectable filler composition. The method can comprise identifying a subject that will benefit from a continuing increase in a volume and/or firmness of a target area during a period following a re-treatment session and continuing for at least 13 months after the re-treatment session. The volume and/or firmness can increase throughout this period. The method can further comprise performing an initial treatment session on the subject. The initial treatment session can comprise a first injection of a nonanimal stabilized hyaluronic acid and thereby provide an increase in volume and/or firmness to the target area. The method can further comprise performing a re-treatment session on the subject. The re-treatment session can comprise a second injection of the nonanimal stabilized hyaluronic acid into the target area at a time subsequent to the initial treatment session. The subject's global aesthetic improvement scale can continue to improve for at least 10.5 months following the re-treatment session. The re-treatment session can occur 2 to 6 months after the initial treatment session. The subject can maintain at least a 1 point improvement in a global aesthetic improvement scale score and/or a wrinkle severity rating score for 18 months after the initial treatment session. In some embodiments, the subject receives no additional injections of said nonanimal stabilized hyaluronic acid to the target area, except for the initial treatment session and the re-treatment session.

In some aspects, the invention comprises a kit for providing a continuing increase in firmness and/or volume from an injectable filler composition. The kit can comprise a dermal filler, a syringe, a needle, and instructions to 1) perform an initial treatment session on a subject. The initial treatment session comprises a first injection of a first injectable filler composition into the subject at a target area, which provides an increase in volume and/or firmness to the target area. The instructions further instruct one to 2) perform a re-treatment session on the subject. The re-treatment session comprises a second injection of a second injectable filler composition into the target area at a time subsequent to the initial treatment session. The second injection extends the increase in volume and/or firmness of the target area. The time subsequent to the initial treatment session is in the range of 1 month to less than 9 months. At least one of the first or second injectable filler compositions comprises hyaluronic acid.

These and other embodiments are described in greater detail below.

BRIEF DESCRIPTION OF THE DRAWINGS

FIG. 1 is a schematic depicting a protocol for a study involving comparison of a re-treatment session after 4.5 months with re-treatment session after 9 months.

FIG. 2 is a table outlining the schedule of procedures for a trial study involving comparison of a re-treatment session after 4.5 months with re-treatment session after 9 months.

FIG. 8 is a graph depicting the percent of subjects with at least one grade of improvement from baseline by visit for the 4.5 month re-treatment.

FIG. 9 is a graph depicting the percent of subjects with at least one grade of improvement from baseline by visit for the 9 month re-treatment.

FIG. 10 is a graph depicting the mean improvement from baseline by visit for the WSRS results for the re-treatment at 4.5 months.

FIG. 11 is a graph depicting the mean improvement from baseline by visit for the WSRS results for the re-treatment at 9 months.

Figure 3:
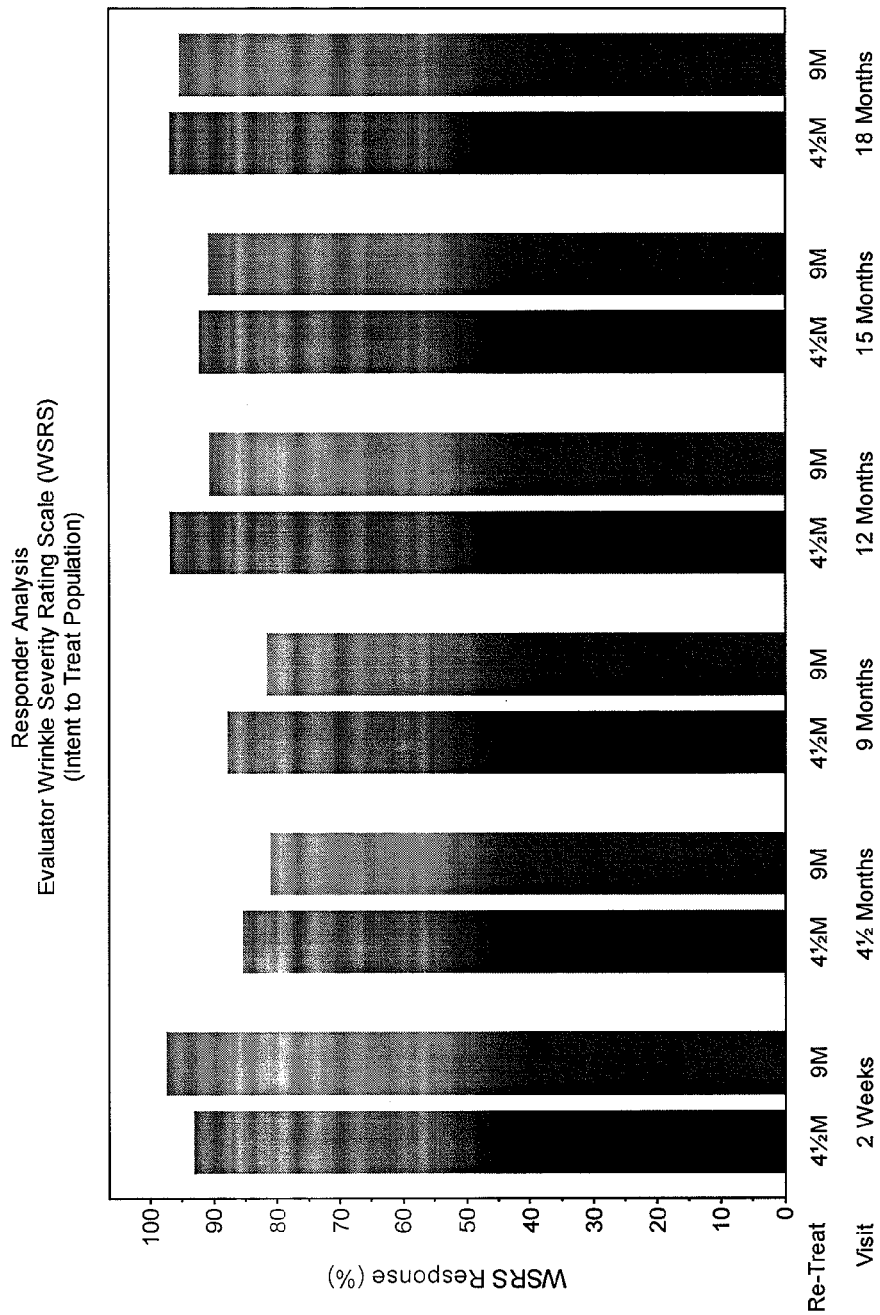
FIG. 3 is a bar graph summarizing results from a trial study. The bar graph shows a comparison of the percent of responders that received a re-treatment session at 4.5 months to the percent of responders that received a re-treatment session after 9 months.

While the subject matter of this application can now be described in detail with reference to the figures, it is done so in connection with the illustrative embodiments. It is intended that changes and modifications can be made to the described embodiments without departing from the true scope and spirit of the subject invention as defined in part by the appended claims.

DETAILED DESCRIPTION OF THE PREFERRED EMBODIMENT

It has now been realized that the standard method of adding volume or firmness to a subject by administering a dermal filler (for example, via a single treatment session), while adequate for some purposes, has various shortcomings. The present disclosure provides various methods for administering dermal fillers, and particularly hyaluronic acid based dermal fillers, to subjects. It has now been discovered that a specific manner of repeated administration of such dermal fillers (a "re-treatment") can result in numerous surprisingly superior results. At a first level, the repeated administration techniques described herein can not only extend the effectiveness of the injectable filler, but actually provide for effectiveness that lasts longer than what would be expected from two independent applications of an injectable filler. Simply put, in some embodiments there is a synergistic result when the described method is employed that provides for results that last for a length of time that is surprisingly long. Furthermore, in some embodiments, the degree or extent of the improvement itself, at various time points following the re-treatment, is also improved over what would ordinarily be expected from two unrelated administrations of a dermal filler; thus, not only is the duration of the benefit extended, but the degree or extent of the benefit itself is also improved. In addition, in some embodiments, the timing of the re-treatment session can allow one to maintain more of the benefits from the injectable filler throughout a continuous period, without losing some of the benefits of the initial treatment session. Furthermore, in some embodiments, the actual amount of dermal filler required to obtain the above surprising and superior results, is surprisingly less than the amount required for two traditional treatment sessions. In some embodiments, not only does the method provide a synergistically long lasting and unexpectedly high level of volume and/or firmness throughout the longer period of time, but such results are achieved with substantially less dermal filler than would be expected for two separate administrations. As described herein, not all of the embodiments will exhibit all of these superior and unexpected results; however, many of the embodiments can exhibit more than one of the above noted surprising and superior results.

In some embodiments, the methods described herein involve applying an injectable filler to correct areas or locations that appear to lack volume or are "under volume," and, at a subsequent time (as a separate treatment session), re-treating the area with the injectable filler composition. As noted below, this retreatment session will occur within a specific time period and/or before the subject might otherwise believe that they would benefit from an additional administration of the injectable filler composition (absent the information provided in the present disclosure). In some embodiments, the re-treatment session is provided within or less than 9 months from the initial treatment session. In addition, in order for the re-treatment session to provide some of the benefits described herein, at least one of the sessions will involve an injectable filler composition that can induce or stimulate collagen production (such as a hyaluronic acid-containing composition). In some embodiments, further surprising and unexpected results can be obtained if the re-treatment session is provided less than 6 months from the initial treatment date. In some embodiments, re-treatment can slow the rate of resorbtion of the injectable filler after re-treatment. In some embodiments, re-treatment can slow the rate of resorbtion of the injectable filler after re-treatment by maintaining tissue expansile tension. Thus, in some embodiments, the re-treatment procedure can provide results lasting for at least 13.5 months if not longer. In some embodiments, little or no loss of volume is observed after about 18 months after initial treatment.

In some embodiments, re-treatment can be performed, for example, prior to the occurrence of an unfavorable change in wrinkle severity in the treated area. One advantage of such an embodiment is that a substantial increase to a subject's baseline wrinkle severity can be avoided throughout a longer duration of time. Thus, in some embodiments, it has been appreciated that the timing of the re-treatment schedule can be such that one can reduce decreases or losses in a first treatment's effectiveness, while still providing for a second treatment (the "re-treatment") in a sufficient period of time to allow for the enhanced duration of effectiveness of the treatment.

It has also been appreciated that many traditional techniques do not take full advantage of the characteristics of volumetric fillers. Thus, some of the disclosed embodiments are useful in allowing one to improve the results of treatment with injectable fillers. In some embodiments, re-treatment provides continued improvement of volume and/or firmness. In some embodiments, the improvement is continuous over a period of time up to about, for example, 13 or 14 months after re-treatment. In some embodiments, the improvement is due at least in part to the stimulation of collagenesis. For example, re-treatment can increase collagen production by fibroblasts. These, and additional aspects, are discussed in greater detail below. However, these aspects are not to be interpreted as limiting upon the claims, unless explicitly recited in the claims themselves.

The present description first describes various terms used in describing various aspects described herein. A general description of various embodiments of the administration methods is then provided and is followed by a more detailed description of specific aspects of the methods and variations. An additional section regarding additional embodiments is then provided. Finally, examples of using the various methods are disclosed.

Definitions and Various Embodiments

The terms "injectable filler composition" and "injectable filler" are used in their ordinary sense as understood by those skilled in the art and thus include a composition that can be administered through injection into or beneath the skin of a subject. The injectable filler composition should not be unduly problematic for the subject receiving the composition. As can be appreciated by one of skill in the art, there are a large number of compositions that can be used as a filler for various embodiments disclosed herein. In some embodiments, the fillers are dermal fillers. In some embodiments, the filler is selected from RESTYLANE® and PERLANE® dermal fillers. Examples of fillers include those disclosed in U.S. Pat. Nos. 5,633,001, 5,007,940, 5,827,937, 5,128,326, 5,399,351, and 5,143,724, as well as PCT Pub. No. WO 87/07898, all of which are herein incorporated by reference in their entireties. In some embodiments, the composition is a cross-linked biocompatible polysaccharide gel composition. In some embodiments, the composition is formed by forming an aqueous solution of a water soluble, cross-linkable polysaccharide; initiating a cross-linking of said polysaccharide in the presence of a polyfunctional cross-linking agent; sterically hindering the cross-linking reaction from being terminating before gelation occurs, an activated polysaccharide thereby being obtained; and reintroducing sterically unhindered conditions for said activated polysaccharide so as to continue the cross-linking thereof up to a viscoelastic gel.

In some embodiments, the injectable filler is characterized by its source. In some embodiments, the source can be biologic and/or synthetic. Biologic injectable fillers can be those that are derived from a living organism. Synthetic injectable fillers can further be divided into two groups, a) man-made fillers for which there is no biologic counterpart and b) man-made substances for which there is a counterpart biologic. In some embodiments, the injectable filler can be characterized by the body's ability to clear a product without external intervention (e.g., these can be biodegradable or nonbiodegradable).

Examples of biologic, biodegradable fillers are those that include materials derived from organism, human, and/or animal tissues and/or products. Examples of such fillers include the following: hyaluronic acid, (such as the following: avian HA, bovine HA, and non-animal stabilized HA ("NASHA", e.g., RESTYLANE® (injectable filler)), collagen (such as collagen I, collagen II, collagen III, cross-linked and/or non-cross-linked, bovine, porcine, human, and autologous collagen). Additional examples of collagen based fillers include ZYPLAST® (collagen derived from bovine tissue), ZYDERM® I (collagen derived from bovine tissue), ZYDERM® II, (collagen derived from bovine tissue), EVOLENCE™ (porcine derived collagen), and FIBREL™ (porcine derived collagen). As can be appreciated by one of skill in the art, in some embodiments, the injectable filler is self-replicating, and can include living cells (such as collagen-producing cells or fibroblasts). Thus, in some embodiments there are injectable fillers that are biological and are relatively long lasting or relatively "permanent."

Synthetic, biodegradable, injectable fillers include RADIANCE™ and RADIESSE™ (microspheres of at least calcium and phosphate ions) injectable fillers, polyacids and polyethers described in U.S. Pat. No. 7,192,984 (e.g., carboxymethyl cellulose (CMC) and polyethylene oxide), and LARESSE® (polymer, polyacid, and/or polyether, similar but not identical to HA type materials).

Synthetic, non-biodegradable, injectable fillers include injectable fillers that are not readily broken down in the body. Synthetic, non-biodegradable, injectable fillers can include injectable fillers that include a biologic component (and vice versa). In some embodiments, at least a portion of product cannot be significantly broken down by various body processes. Additional examples of synthetic non-biodegradable fillers include the following: ARTEFIL™ (polymethylmethacrylate (PMMA) microspheres suspended in bovine collagen), ARTECOL™ (polymethylmethacrylate (PMMA) microspheres suspended in bovine collagen), polymethylmethacrylate (Plexiglas) in bovine collagen carrier, denatured, silicone, and various polymers, polyacids, and polyethers. In some embodiments, the carrier has rapid biodegradation. Of course, as can be appreciated by one of skill in the art, in some embodiments, any one, combination, or ingredient of the above fillers can be combined with the other fillers (or alternative fillers) in various embodiments and for particular results.

As can be appreciated by one of skill in the art, injectable fillers need not be categorized by both their source and their ability to stay or be cleared from the body. That is, some fillers can simply be biological, synthetic, biodegradable, or non-biodegradable. Additionally, as can be appreciated by one of skill in the art, some injectable fillers can include parts or aspects of various combinations of the above or following substances.

Examples of injectable fillers include a substance selected from the following: collagen, fat, human or animal derived collagen, bovine collagen, type I collagen, type II collagen, type III collagen, 3.5% bovine dermal collagen cross-linked by glutaraldehyde to form a latticework, natural human collagen, autologous collagen, polymethylmethacrylate microspheres (optionally suspended in bovine collagen), suspension of collagen fibers prepared from the subject's tissue, human tissue collagen matrix derived from cadaveric dermis, the polyacids and polyethers described in U.S. Pat. No. 7,192,984 (e.g., carboxymethyl cellulose (CMC) and polyethylene oxide), acellular human cadaveric dermis that has been freeze-dried, micronized acellular human cadaveric dermis that has been freeze-dried, cultured autologous fibroblasts, hyaluronic acid, non-animal-stabilized hyaluronic acid derivative, microspheres of calcium hydroxyl appetite suspended in an aqueous gel carrier, dextran beads suspended in hylan gel of nonanimal origin (e.g., 40- to 60-µm in diameter), solubilized elastin peptides with bovine collagen, silicone, solubilized elastin peptides with bovine collagen, poly-L-lactic acid, Gore-Tex (PTFE), glycosylated collagen, PMMA, bone-forming calcium apatite, cultured human cells, expanded polytetrafluoroethylene (e-PTFE), SOFTFORM® of ePTFE, and some combination thereof. Further examples of injectable fillers include the following: AQUAMID® (comprising water and cross-linked polymers), ARTEFIL® (polymethylmethacrylate (PMMA) microspheres suspended in bovine collagen), LARESSE® Dermal Filler (synthetic, biocompatible polymers, non-HA gel comprising absorbable medical polymers), ARTECOLL® (polymethylmethacrylate (PMMA) microspheres suspended in bovine collagen), BELOTERO®, BIO-ALCAMID™ (synthetic reticulate polymer (poly-alkyl-imide), CAPTIQUE™ (non-animal hyaluronic acid), COSMODERM™ (human collagen skin filler), COMOPLAST™, CYMETRA®, autologen, DERMALOGEN®, FASCIAN™ (fascia), fascia, fat, Hylaform™ (avian hyaluronic acid), JUVEDERM® (biosynthesized, non-animal hyaluronic acid), RADIESSE™ (microspheres of at least calcium and phosphate ions), SCULPTRA® (poly-L-lactic acid (PLLA)), collagen, hyaluronic acid, RESTYLANE®, PERLANE®, ZYDERM®, ZYPLAST® (collagen derived from bovine tissue), DERMALIVE®, (hyaluronic acid and acrylic hydrogel particles), DERMADEEP® (hyaluronic acid and acrylic hydrogel particles), HYDRAFILL®, ISOLAGEN® (cultured autologous human fibroblasts), LARESSE® (carboxymethylcellulose (CMC) and polyethylene oxide (PEO) filler), PURAGEN™ (filler comprising double cross-linked hyaluron molecules), REVIDERM® INTRA (filler comprising flexible dextran micro-beads suspended in super-coiled, stabilized hyaluronic acid), SCULPTRA™ (Formerly NEW-FILL™, filler from poly-L-lactic acid), Teosyal, SURGIDERM® (hyaluronic acid filler involving 3D hyaluronic acid matrix technology), OUTLINE®, ANIKA®, Cosmetic tissue augmentation (CTA, from Anika), and combinations thereof.

As can be appreciated by one of skill in the art, any of the above fillers or components thereof can include other materials, for example, anesthetic materials, including, without limitation, lidocaine, prilocalne, tetracaine, etc.

"Volumetric filler" is a type of injectable filler composition. Volumetric fillers can be dermal fillers. In some embodiments, the volumetric filler is capable of crosslinking and/or is cross-linked. Cross-linked compositions allow the filler to have predictably no or minimal volume or substance loss on injection. In some embodiments they also provide predictable expansion or "swelling" with re-hydration on injection: swelling to no more than 10% volume increase; not "shrinking" or losing volume as some fillers that lose water uncrosslinked HA volumes; and/or have sufficient tensile compression resistance. In some embodiments, the volumetric filler involves microbead technology (e.g., as disclosed in U.S. Pat. Nos. 5,633,001 and 5,007,040, herein incorporated by reference in their entireties). In some embodiments, this allows compression resistance. In some embodiments this allows for the composition to have the ability to resist displacement. Other fillers, described as "slurries," can be used but can be prone to displacement (e.g., disclosed in U.S. Pat. Nos. 5,143,724, 5,633,001, herein incorporated by reference in their entireties). In some embodiments, the filler has the biocompatibility and "feel" of tissue rather than bony implants or sedimentary products that can feel hard. However, bony implant or sedimentary fillers can also be used in some embodiments.

"Dermal filler" is a type of injectable filler composition. Dermal filler denotes that the filler is compatible for use in or under the skin. Dermal fillers can be volumetric fillers. In some embodiments, the dermal filler composition comprises, consists, or consists essentially of a hyaluronic acid or hyaluronic acid derivative. The term "hyaluronic acid" includes salts and bases thereof. In some embodiments, the hyaluronic acid comprises a nonanimal stabilized hyaluronic acid, including gels thereof. In some embodiments, the hyaluronic acid comprises avian HA, bovine HA, or human HA (e.g., RESTYLANE® and PERLANE® injectable fillers)). In some embodiments, the hyaluronic acid comprises at least one of CAPTIQUE™ (non-animal hyaluronic acid), HYLAFORM™ (avian hyaluronic acid), JUVEDERM® (biosynthesized, non-animal hyaluronic acid), DERMALIVE®, (hyaluronic acid and acrylic hydrogel particles), DERMADEEP® (hyaluronic acid and acrylic hydrogel particles), HYDRAFILL®, PURAGEN™ (filler comprising double cross-linked hyaluron molecules), and/or REVIDERM® INTRA (filler comprising flexible DEXTRAN micro-beads suspended in super-coiled, stabilized hyaluronic acid).

The term "extend" in reference to an improvement of firmness and/or volume denotes that the duration, degree, or duration and degree of the improvement has been increased or "extended". Thus, in this context the term "extend" can refer to an extension in the amount of time that the improvement is present, and the term "extend" can also denote that the size of the improvement, either overall or at a specific point in time, has also increased. Of course, the term can denote both of these aspects at once as well.

The term "improvement" in reference to firmness and/or volume denotes that there has been an increase in the apparent firmness of a subject's skin that has received the injectable filler and/or that there has been an apparent increase in the volume of an under volume area. One example of an increase in volume would include the removal or diminution of lines, wrinkles, and/or undervolume areas in the subject's skin. In some embodiments, an improvement in firmness and/or volume can be described by using the Wrinkle Severity Rating Scale ("WSRS"). Values can be assigned as follows: 1—Absent, 2—Mild, 3—Moderate, 4—Severe, and 5—Extreme. Thus, a decrease in the WSRS can denote an improvement in volume and/or firmness. Of course, the larger the decrease, the larger the improvement in volume and/or firmness. In some embodiments, an improvement in firmness and/or volume can be described by the Global Aesthetic Improvement Scale ("GAIS"), which can have values assigned as follows: 0—Worse; 1—No Change; 2—Improved; 3—Much Improved; and 4—Very Much Improved. In such a scale, the larger the increase, the larger the improvement in volume and/or firmness. Of course, in some embodiments, changes in volume and/or firmness can be characterized simply as a change in volume and/or firmness, without using either the WSRS or the GAIS. The skilled in the art will appreciate that the determination of a WSRS or GAIS score is made by a trained evaluator.

In some embodiments, the methods described herein are used to alter the appearance of a subject's face. In some embodiments, this alteration is purely an aesthetic alteration. In some embodiments, the alteration does not treat or adjust any deformity that the subject may have. For example, in some embodiments, the subject may simply want added volume to various areas of their face. As such, the application of filler will not necessarily be considered a treatment of the subject's face in all embodiments. Additionally, the term "under volume" does not imply or require that there is necessarily a deformity in the subject's face. Rather, it simply denotes that there appears to be less volume under the skin in one area than in another. In some embodiments, the filler and technique is applied as a treatment of a deformity in a patient. Such applications can be more specifically denoted by the recitation of the fact that a "deformity" is being "treated," or by the fact that the subject is called a "patient." Applications in which no deformity is being addressed can be more specifically denoted by the use of the terms "non-treatment," "subject-preference" or similar term. When such terms are not explicitly used, the techniques and aspects are generic to both treatment and non-treatment applications. As will be appreciated by one of skill in the art, the term "subject" encompasses "patient." In some embodiments, the method is used to reduce or reverse the signs of aging.

"Target area" as used herein refers to areas or locations to be treated with injectable filler composition, and includes areas or locations that appear to lack volume or are "under volume." "Target areas" include locations of, for example, oral commissures, marionette lines, mandibular hollows, raise jowls, frowning mouth, pouty lower lip, lateral expression lines, mental creases, chin dimplings, zygomatic hollows, nasolabial folds, tear troughs, malar area or prominence, and brow lifts.

As noted above, the term "treatment" can denote a purely cosmetic result and one that can remove or reduce signs of aging.

In general, the term "initial treatment" or "initial treatment session" denotes the application of an injectable filler to a location that does not currently retain a significant amount of an exogenous injectable filler. As will be appreciated by one of skill in the art, an initial treatment can be performed to achieve a "full correction" of a location. In some situations, this initial treatment can include a "touch-up" application, approximately one to two weeks after the initial injection session. As will be appreciated by one of skill in the art, the touch-up application is a step that is done as part of the initial treatment session and performed to bring the subject's appearance into full correction. This is typically done after the swelling in the subject's face has gone down (due to the initial application of the injectable filler) but before the benefits of the initial injections are lost. Generally, the term "initial treatment" will include both the initial injection(s) (or the "initial injection session") and, if needed, a subsequent injection (or set thereof) described as a "touch-up" application or injection. As will be appreciated by one of skill in the art, the touch-up application is designed to bring the treated area into full correction. Thus, in situations where the "initial application" of the dermal filler brings the area into full correction, no touch-up application is required. In addition, in some embodiments a touch-up application generally involves the application of a smaller amount of a dermal filler compared to the initial injections of the dermal filler. For example, in some embodiments, the volume of dermal filler applied during the initial injection session is more than 0.5 cc per side of a subject's face, for example, 0.5-0.6, 0.6-0.7, 0.7-0.8, 0.8-0.9, 0.9-1, 1-1.1, 1.1-1.2 cc or more (e.g., 1-2, 2-3, 3-4, 4-5 cc, or more). The volume of dermal filler applied during the touch-up application is generally less, e.g., approximately 0.2 to 0.3, 0.3-0.4, 0.4-0.5, 0.5-0.6, 0.6-0.7 cc (for each side of a subject's face). For the purposes of the timing of the initial treatment session ("ITS") and subsequent steps, the ITS will be described as occurring as of the initial injection session, even if there is a touch-up application two weeks later. Thus, if a re-treatment occurs 4.5 months after an ITS, it is the initial injection session that occurred 4.5 months before the re-treatment session, and if any touch-up application occurred, it could have happened 4 months prior to the re-treatment session (assuming the touch-up application occurred two weeks after the initial injection session).

The term "re-treatment" or "second treatment" session denotes an application of an injectable filler that is distinct from the initial treatment session (e.g., the initial injection session and, optionally, the touch-up application) and occurs following a full-correction of the location that the injectable filler is applied to. The re-treatment occurs after the full correction has been achieved and is performed prior to the complete degradation of the product from the initial treatment. In some embodiments, the re-treatment is applied two months after the initial treatment. In some embodiments, the re-treatment occurs following the degradation of the dermal filler from the initial treatment. In some embodiments, the re-treatment occurs after any touch-up application and thus can be more than 0.5 months after the initial injection session. In some embodiments, re-treatment session occurs 2-3, 3-4, 4-5, 5-6, 6-7, 7-8, 8-9, 9-10, 10-11, 11-12 or more months following the initial treatment. In some embodiments, the re-treatment occurs following the initial treatment, but after the volume of the dermal filler that was applied to the subject has decreased, thereby allowing additional dermal filler to be added to the subject. While the volume can vary, the average volume applied for the re-treatment can be 0.3 cc or greater, for example, 0.3-0.4, 0.4-0.5, 0.5-0.6, 0.6-0.7, 0.7-0.8, 0.9-1, 1-1.1 cc or greater, for each side of a subject's face. As will be appreciated by one of skill in the art, in some embodiments, the "re-treatment" can occur after any number of previous initial treatments or re-treatments. Thus, in some embodiments, a subject undergoes more than one re-treatment (each appropriately timed with respect to one another). In some embodiments, the subject undergoes 2, 3, 4, 5, 6, 7, 8, 9, 10, or more re-treatment sessions. In such embodiments, the previous "re-treatment" is considered to be an "initial treatment session" as far as the timing of the applications is concerned. Thus, a subject can receive an initial treatment session at time zero, a first re-treatment at 4.5 months, and then an additional retreatment session at any point more than one month after the first re-treatment session. Of course, as the results following the initial retreatment session are especially long lived and effective, in many cases subsequent re-treatment applications are not required for at least 13.5 months. In some embodiments, the re-treatment only occurs after the very first treatment session, and any subsequent application of the methods described herein will commence after the subject's appearance has returned to its initial (pre-initial treatment session) volume and/or firmness.

As will be appreciated by one of skill in the art, the "touch-up" application is distinct from a second or re-treatment session. The touch-up application is used in order to first achieve a desired result and typically occurs within one or two weeks of the initial injection. The touch up application is not used to extend an effect of HA, nor do those skilled in the art characterize it as such, as a touch-up application is used to achieve the desired result in the first place (e.g., a full correction). In contrast, as noted herein, the re-treatment session occurs after the time period that a touch-up application would occur and results in an extended improvement of the effects of HA (which can be part of the initial treatment session, the re-treatment session, or both sessions). In some embodiments, a re-treatment session will occur after the subject has received a full correction.

In some embodiments, the volume of the dermal filler for the initial injection session is greater than the volume used in the re-treatment session, which is greater than the optional volume used in the touch-up application.

A "full correction" denotes that the volume desired has been achieved in the subject's skin due to the presence of the dermal filler (e.g., excluding swelling from the application of the dermal fillers).

Various Embodiments

While the current use of hyaluronic acid dermal fillers can provide effective and desirable increases in volume and/or firmness for many subjects, the results are not permanent and eventually the increases in volume and/or firmness decline. Of course, once the results of the treatment decline sufficiently, the subjects will frequently develop a desire to undergo a new round of treatment.

The present disclosure demonstrates that, rather than waiting to begin a completely new round of treatment, there are significant advantages to using an appropriately timed treatment regime. Such "re-treatment" methods can result in surprisingly effective extended effects, with subjects retaining high levels of improvements in volume and/or firmness for 9, 10, 11, 12, 13 months and longer. Furthermore, as described herein early re-treatment can be superior as patients can reduce any increase in wrinkle severity before receiving a second treatment. Furthermore, in some embodiments, to achieve the above surprising and superior results, the amount of injectable filler employed in the re-treatment session can be surprisingly low, in order to achieve the above noted surprising and superior results.

In some embodiments, the method includes an initial treatment session, followed by a re-treatment session within less than 9 months of the initial treatment session. In some embodiments, for even greater surprising and superior results, the re-treatment session occurs within less than 6 months from the initial treatment session. While different injectable fillers can be used for the two different sessions, in an embodiment at least one of the sessions (and optimally both) will include hyaluronic acid (e.g., a NASHA) as the injectable filler.

Figure 4:
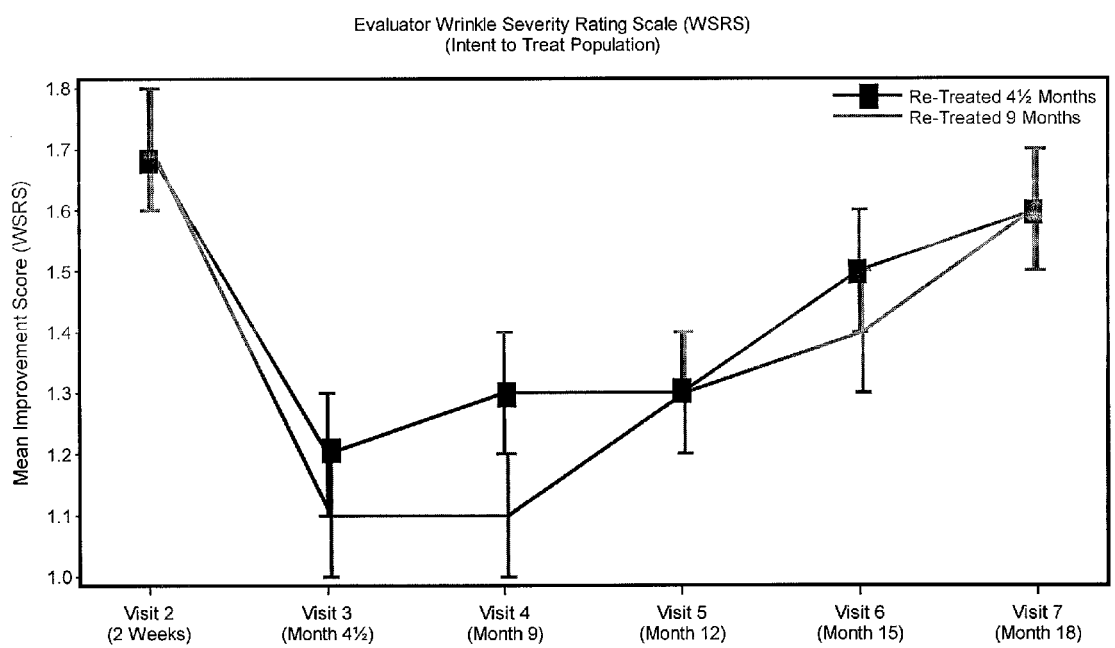
FIG. 4 is a line graph summarizing results from a trial study. The line graph shows a comparison of the improvement resulting from re-treatment at 4.5 months with re-treatment after 9 months at the indicated time points.

While the numerous surprising and unexpected results are discussed in more detail below and in the examples, the results shown in FIG. 4 (as well as Tables 5.7 and 5.8) demonstrate one especially interesting difference between what occurs in a traditional single session treatment and what occurs in some of the present re-treatment embodiments. As will be appreciated by one of skill in the art, while the effectiveness of a single treatment of a dermal filler will slowly decline after the administration of the injectable filler (see, e.g., FIG. 4), the effect of these embodiments results in a steady, long lasting effect, and by some measures, actually results in a gradual and prolonged increase in the WSRS and/or GAIS scores following the re-treatment session. As shown in FIG. 4, counterintuitively, the more time that passes from the re-treatment event (either at 4.5 or 9 months), the greater the improvement (shown as an increase in the improvement). Similarly, as shown in Tables 5.7 and 5.8, the GAIS scores continue to increase as time passes from the re-treatment session. Thus, it appears that while a single treatment session may provide relatively short lived results that operate by a mechanism that slowly dissipates over time, it appears that at least some of the re-treatment embodiments operate by a different mechanism, one that maintains and even gradually improves over time. Surprisingly, this dramatic reversal is achieved by applying another application of the dermal filler, within a specified time period, as described herein. Thus, the presently disclosed re-treatment method is not merely providing a second round of a previous treatment, but in some embodiments, provides numerous surprising and unexpected advantages by a mechanism that appears to be fundamentally different from the mechanism underlying the current single treatment session.

Some of the disclosed embodiments are useful for maintaining, prolonging, extending, and/or improving the results of treatment with injectable fillers. In some embodiments, methods involve, for example: treating, with injectable filler, areas that appear to be "under volume" in a subject; optionally touching-up any areas as needed within, for example, one to two weeks of the initial treatment; and re-treating the subject with injectable filler at an appropriate interval following the initial treatment session. Such a method can greatly extend the duration of benefit obtained from an injectable filler. For example, in some embodiments, the use of a re-treatment step allows for the benefits to be extended for more than 6, 7, 8, 9, 10, 11, 12, 13 months or more. In some embodiments, at least one of the treatment sessions will include an injectable filler that includes HA. In some embodiments, both sessions will include HA.

In some embodiments, the re-treatment session can occur relatively close in time to the initial treatment session so that subjects do not experience an increase in wrinkle severity before receiving the re-treatment, which can still allow for the prolonged benefits of the dual treatment method described herein. Without intending to be limited by theory, the dual session treatment process is believed to maintain tissue expansile tension and slow gel resorption so that benefits and duration of effectiveness of the injections can be extended (and appear the same when comparing re-treatment durations of 4.5 months and 9 months, as described in the examples).

In some embodiments, a subject can be treated with injectable filler to correct areas or locations that appear to lack volume or are "under volume," and, at a subsequent time, the same areas or locations can be re-treated with injectable filler. In some embodiments, a third, fourth, fifth, or additional treatments with injectable filler can be performed. In various embodiments, a time course of treatments can be determined, for example, by evaluation of treatment outcome at various time points. The evaluation can be performed during, for example, follow-up sessions.

The injectable fillers used can be any injectable filler suitable for correcting areas or location that appear to lack volume. Examples of injectable fillers are provided in the previous section and include, for example without limitation, volumetric fillers and dermal fillers. In some embodiments, the injectable filler can be, for example, RESTYLANE® dermal filler. In some embodiments, the injectable filler used for the initial treatment can be the same as the injectable filler used for re-treatment. For at least one of the treatment sessions in some embodiments, at least one of the injectable fillers will stimulate collagen synthesis. This filler can comprise, for example, HA.

In some embodiments, the injectable fillers used for the initial treatment and re-treatment are different. In cases where the injectable fillers used to re-treat is different from the injectable filler used for the initial treatment, the injectable fillers used to re-treat can improve the efficacy of the injectable filler used for the initial treatment. In some embodiments, the injectable filler comprises a substance such as hyaluronic acid.

In some embodiments, the initial treatment and the re-treatment employ a same or similar substance as the injectable filler. In some embodiments, the initial treatment employs a HA substance and the re-treatment employs any injectable filler. In some embodiments, the initial treatment employs any injectable filler and the re-treatment employs an HA substance. In some embodiments, the HA is 100,000 gel particles/ml filler. In some embodiments, the initial treatment and re-treatment employ injectable fillers that do not include HA. In some embodiments the filler for the initial injection session and the touch-up application are the same type of injectable filler. In some embodiments the injectable filler for the initial injection session and the touch-up application are different types of injectable fillers. In some embodiments, the touch-up dermal filler is HA. In some embodiments, the filler for the initial treatment allows for expansion of the tissue while also being capable of being absorbed into the skin or degraded.

In some embodiments, the hyaluronic acid is generated by a Streptococcus species of bacteria. In some embodiments, the hyaluronic acid is stabilized, e.g., non-animal stabilized. In some embodiments, the hyaluronic acid is chemically crosslinked with BDDE (1,4 butanediol diglycidyl ether), stabilized (e.g., NASHA), and suspended in phosphate buffered saline at a pH of 7 and a concentration of 20 mg/ml. In some embodiments, the hyaluronic acid is free of animal protein. For example, in an embodiment, the hyaluronic acid is a gel generated by a Streptococcus species of bacteria, chemically cross-linked with BDDE, stabilized, and suspended in saline at pH 7 (e.g., as in RESTYLANE® dermal filler, RESTYLANE TOUCH™ dermal filler, RESTYLANE FINE LINES™ dermal filler, RESTYLANE VITAL™ dermal filler, and RESTYLANE LIPP™ dermal filler). Such embodiment may be in a concentration of 20 mg/ml, phosphate buffered at pH 7, and/or free of animal protein. In some embodiments, the hyaluronic acid is one that is suitable for injection into a dermal location where it acts to stimulate collagen synthesis.

In some embodiments, the hyaluronic acid is in the form of gel particles. In some embodiments, the hyaluronic acid is in the form of gel particles having sizes in the range of about 940 microns to about 1090 microns. In some embodiments, the largest fraction of gel particles size is between 940 microns and 1090 microns (e.g., as in PERLANE® dermal filler). In some embodiments, the hyaluronic acid gel particles have a particle size that is less than 1200 microns. In some embodiments, the hyaluronic acid gel particles have a particle size that is about 400 microns. In some embodiments, the hyaluronic acid gel particles have a particle size that is less than 400 microns. In some embodiments, the hyaluronic acid gel particles have a particle size that is more than 400 microns. In some embodiments, the hyaluronic acid gel particles have a particle size that is in the range of about 400 to about 1200 microns.

The concentration of hyaluronic acid gel particles in the dermal filler may vary over a broad range, e.g., about 500-200,000 particles per mL, such as about 500-5000 particles per ml, about 5,000-50,000 particles per ml, about 50,000-150,000 particles per ml, or about 150,000-200,000 particles per ml. For example, in some embodiments, the dermal filler comprises about 200,000 hyaluronic acid gel particles per ml (e.g., as in RESTYLANE FINE LINES™ dermal filler and RESTYLANE TOUCH™ dermal filler). In some embodiments, the dermal filler comprises about 100,000 hyaluronic acid gel particles per ml (e.g., as in RESTYLANE® dermal filler). In some embodiments, the dermal filler comprises about 10,000 hyaluronic acid gel particles per ml (e.g., as in PERLANE® dermal filler). In some embodiments, the dermal filler comprises about 1,000 hyaluronic acid gel particles per ml (e.g., as in RESTYLANE SUBQ™ dermal filler). The package inserts for RESTYLANE® dermal filler and PERLANE® dermal filler are hereby incorporated by reference in their entireties, and particularly for the purpose of describing those brands of dermal filler products.

In some embodiments, the hyaluronic acid composition comprises a cross-linked biocompatible polysaccharide gel composition, which is obtainable by cross-linking a cross-linkable polysaccharide with a polyfunctional cross-linking agent in two steps, the first cross-linking step can be terminated before gelation occurs by a sterical hindrance of the cross-linking reaction. The second cross-linking step can be initiated by reintroducing sterically unhindered conditions for the cross-linking reaction. This reaction can continue up to a viscoelastic gel, wherein the gel composition exhibits retained biocompatibility, viscoelasticity and does not swell substantially when placed in contact with water. In some embodiments, the stabilized hyaluronic acid composition is that disclosed in U.S. Pat. No. 5,827,937, hereby incorporated by reference in its entirety and particularly for the purpose of describing hyaluronic acid compositions and methods of making them.

In some embodiments, the stabilized hyaluronic acid can be prepared as described in U.S. Pat. No. 5,827,937. In some embodiments, this process can include the following steps: forming an aqueous solution of a water soluble, cross-linkable polysaccharide; initiating a cross-linking of said polysaccharide in the presence of a polyfunctional cross-linking agent therefor; sterically hindering the cross-linking reaction from being terminated before gelation occurs (thereby obtaining an activated poly-saccharide); and reintroducing sterically unhindered conditions for said activated polysaccharide so as to continue the cross-linking thereof. In some embodiments, the process involves a cross-linking of a water-soluble, cross-linkable polysaccharide in at least two steps or stages, where the cross-linking reaction is discontinued before the galation is initiated. The discontinuance can be accomplished by sterically hindering the cross-linking reaction. The cross-linking reaction can then be continued in a second step by reintroducing sterically unhindered conditions. Any known cross-linking agent can be used, if it is useful in connection with polysaccharides, consideration being taken to ensure that the biocompatibility prerequisites are fulfilled. Preferably, however, the cross-linking agent is selected from the group consisting of aldehydes, epoxides, polyaziridyl compounds, glycidyl ethers and dividylsulfones. Of these glycidyl ethers represent an especially preferred group, of which 1,4-butandiol digylcidylether can be referred to as a preferred example. The initial cross-linking reaction in the presence of a polyfunctional cross-linking agent can be performed at varying pH values, primarily depending on whether ether or ester reactions should be promoted. Preferably this means that said cross-linking reaction is performed at an alkaline pH, especially above pH 9, e.g. in the range of pH 9-12, when promoting ether formations. When promoting ester formations said cross-linking reaction is preferably performed at an acidic pH, especially at pH 2-6. In some embodiments, the activation of the polymer can occur under alkaline conditions and as follows: 10 g of hyaluronic acid from Streptococcus can be dissolved in 100 ml of 1% NaOH pH>9. Cross-linking agent in the form of 1,4-butandiol diglycidylether can be added to a concentration of 0.2%. The solution can be incubated at 40 degrees Celsius for 4 hours. In some embodiments, the activation of the polymer can occur under acidic conditions and as follows: similar as above, but at an acidic pH of about 2-6 by the addition of 1% of acetic acid to the solution instead of NaOH.

Some of the indications which can be addressed by the systems and methods disclosed herein include: oral commissure, marionette lines, mandibular hollow, raise jowl, frowning mouth, pout lower lip, later expression lines, mental crease, chin dimpling, zygomatic hollow, nasolabial folds, tear trough, and brow lift.

In various embodiments, the objective of the initial treatment can be to achieve a desired cosmetic result at the areas of treatment. In some embodiments, defects (i.e., areas or locations that appear to lack volume or are "under volume") can be fully corrected during an initial treatment session. The amount of correction may be ascertained by visual assessment of appearance of the defect. In some embodiments, the amount of correction can be determined with the aid of, for example, a Severity Rating Scale, such as that shown in Table 0.1.

TABLE 0.1

Severity Rating Scale

| Score | Description |
|---|---|
| 5 | Extreme: Extremely deep and long folds; detrimental to facial appearance. 2-4 mm visible v-shaped fold when stretched. Unlikely to have satisfactory correction with injectable implant alone. |
| 4 | Severe: Very long and deep folds; prominent facial feature. Less than 2 mm visible fold when stretched. Significant improvement is expected from injectable implant |
| 3 | Moderate: Moderately deep folds; clear facial feature visible at normal appearance but not when stretched. Excellent correction is expected from injectable implant. |
| 2 | Mild: Shallow but visible fold with a slight indentation; minor facial feature. Implant is expected to produce a slight improvement in appearance. |
| 1 | Absent: no visible fold; continuous skin line |

For example, a severity rating of 1 on the severity scale provided above can indicate full correction of a defect. In various embodiments, overcorrection can be undesirable. In various embodiments, treatment and/or re-treatment can correct defects from about 90% to about 100%. Preferably, a maximum of about 100% correction should be administered, without overcorrection, at each treatment.

In some embodiments, the injection site can be massaged to conform to the contour of the surrounding tissues.

In some embodiments, the amount of filler composition administered at each session for any target area can be in the range of from about 0.01 cc to about 1 cc, for example 0.01-0.05, 0.05-0.1, 0.1-0.15, 0.15-0.2, 0.2-0.3, 0.3-0.4, 0.4-0.5, 0.5-0.6, 0.6-0.7, 0.7-0.8, 0.8-0.9, or 0.9-1 cc. In some embodiments, each treatment site can be treated with, for example, a maximum dosage of about 1-2, 2-3, 3-4, 4-5 cc per treatment session. If the treated area is swollen directly after the injection, melting ice can be applied on the site for a short period. The subject can be evaluated post treatment, which is described in more detail below. In some embodiments, photographs can be taken prior to each treatment. In some embodiments, the photography can be done in accordance with, for example, the standard Canfield system.

In some embodiments, the amount of injectable filler administered during the re-treatment session is equal to or less than the amount administered in the first treatment session (which can optionally include a touch-up application). In some embodiments, the amount of filler employed in the re-treatment session is less than 100% of the amount employed for the initial treatment session, for example, 99, 98, 95, 90, 85, 80, 75, 70, 65, 60, 55, 50, 45, 40, 35, 30, 25, 20, 15, 10 percent of the amount employed in the initial treatment session, including any range below any of the preceding values and any amount defined between any two of the preceding values. In some embodiments, the amount employed in the re-treatment session is approximately 0.01-0.05, 0.05-0.1, 0.1-0.15, 0.15-0.2, 0.2-0.3, 0.3-0.4, or 0.4-0.5 cc for any given target area. In some embodiments, the total amount administered for the re-treatment session is between 1 and 2.5 cc.

Re-treatment can be performed after the initial treatment. In some embodiments, re-treatment can be performed prior to observation of an unfavourable change in aesthetic improvement. In some embodiments, re-treatment can be performed before an unfavourable change in severity rating according to the Severity Rating Scale occurs. In some embodiments, re-treatment is performed between 1 months and 9 months after the initial treatment. In some embodiments, a re-treatment can be performed about 1 and about 6 months after an initial treatment. In some embodiments, a re-treatment can be scheduled for about 1-2, 2-2.5, 2.5-3, 3-3.5, 3.5-4, 4-4.5, 4.5-5, 5-5.5, 5.5-6, 6-6.5, 6.5-7, 7-7.5, 7.5-8, 8-8.5, 8.5-9 or more months after an initial treatment. Subsequent re-treatments may be performed at any time point subsequent to the previous treatment. In some embodiments, re-treatment is performed, for example, about one month to about 9 months after a previous treatment session, (either an initial treatment or a subsequent re-treatment). In some embodiments, this re-treatment session following any previous treatment session, is 1-9, 1-6, 2-9, 2-6, 2-5, 2-4, 3-5, 4-5, or about 4.5 months after the previous treatment.

As noted above and demonstrated in the examples below, in some embodiments, the use of a re-treatment session allows for a surprisingly long duration of effectiveness. In some embodiments, the duration of effectiveness of the dermal filler increases by at least 5%, for example, 6, 7, 8, 9, 10, 15, 20, 25, 30, 35, 40, 45, 50, 55, 60, 65, 70, 75, 80, 85, 90, 95, 100, 110, 120, 130, 140, 150 percent or more (including any range above any of the preceding values and any amount defined between any two of the preceding values). In some embodiments, the re-treatment session allows for a surprisingly long duration of effectiveness that is at least 6 months, for example, 7, 8, 9, 10, 11, 12, 13, 14 or more months of effectiveness.

In some embodiments, after an initial application of a HA filler and using a re-treatment process, the duration of effectiveness will be 18 months from the initial treatment session. In some embodiments, using a RESTYLANE® dermal filler in one of the present re-treatment embodiments results in an overall duration of effectiveness of 18 months from the initial treatment session. In some embodiments, the duration of effectiveness will be at least 6 months from the re-treatment session, for example at least 7, 8, 9, 10, 11, 12, 13, 14 or more months from the re-treatment session. In some embodiments, the effectiveness is measured in terms of subject satisfaction with the results. In some embodiments, the effectiveness is measured as at least one point or level of improvement for one of the two scales described herein (WSRS and GAIS).

In some embodiments, administering a re-treatment session less than 6 months from the initial treatment session allows for the above advantage to occur and further allows one to maintain a relatively high level of improvement throughout the duration following the retreatment session. As will be appreciated by one of skill in the art, prior to the present disclosure, it would have been counterintuitive to apply an additional administration of an injectable filler when there was no apparent need to supply such an additional amount of an injectable filler. However, by performing the re-treatment session well before 9 months, preferably 2 to 6 months after the initial treatment session, one not only still obtains the superior long lasting effects identified above, but does so without the dip in WSRS that would have otherwise been present, had one waited for 9 months. Thus, not only is applying the re-treatment session within this time zone (1 to less than 6 months) counterintuitive (as there is no reason to apply it), it is also superior, even over the above noted advantages, as it avoids or lessens any decrease in results of the injectable filler composition.

In some embodiments, providing the re-treatment session between 1 and less than 6 months, allows one to maintain at least 1 grade of improvement in the subject's WSRS. In some embodiments, at least 1.1, 1.2, 1.3, 1.4, 1.5, 1.6, 1.7, or 1.8 points of improvement are maintained throughout an 18 month period. In some embodiments, the above technique allows for the subject to maintain the improvement for a longer part or duration of the time following the re-treatment session. As will be appreciated by one of skill in the art, the present fractional mean values are most applicable in describing a population of (e.g., two or more) subjects. Thus, in some embodiments, these mean values can be measured across a population of subjects that is being treated. One example of the treatment of a population includes performing an initial treatment session on a population of subjects, where the initial treatment session comprises a first injection of a first injectable filler composition into each of the subjects of the population at a target area in each of the subjects, thereby providing an increase in volume and/or firmness to the target areas. The method can further include performing a re-treatment session on the population of subjects. The re-treatment session comprises a second injection of a second injectable filler composition into the target areas at a time subsequent to the initial treatment session.

In some embodiments, for at least 10% of a 13.5 month period following the re-treatment, the subject (or population) will have mean improvement score of at least 1, 1.1, 1.2, 1.3, 1.4, 1.5, 1.55, or 1.6 to the subject's WSRS, or will have a mean WSRS of no more than 1.9 (e.g., no more than 2.2, 1.9, 1.8, or 1.7).

In some embodiments, for at least 25% of a 13.5 month period following the re-treatment, the subject (or population) will have mean improvement score of at least 1, 1.1, 1.2, 1.3, 1.4, 1.5, or 1.6 to the subject's WSRS, or will have a mean WSRS of no more than 2 (e.g., no more than 1.9, 1.8, or 1.7).

In some embodiments, for at least 33% of a 13.5 month period following the re-treatment, the subject (or population) will have mean improvement score of at least 1, 1.1, 1.2, 1.3, 1.4, 1.5, or 1.6 to the subject's (or population's) WSRS, or will have a mean WSRS of no more than 2.05 (e.g., no more than 2, 1.9, 1.8, or 1.7).

In some embodiments, for at least 50% of a 13.5 month period following the re-treatment, the subject (or population) will have mean improvement score of at least 1.3, 1.4, 1.5, or 1.6 to the subject's (or population's) WSRS or will have a mean WSRS of no more than 2.1 (e.g., no more than 2, 1.9, 1.8, or 1.7).

In some embodiments, for at least 75% of a 13.5 month period following the re-treatment, the subject (or population) will have mean improvement score of at least 1.3, 1.4, 1.5, or 1.6 to the subject's (or population's) WSRS, or will have a mean WSRS of no more than 2.1 (e.g., no more than 2, 1.9, 1.8, or 1.7).

In some embodiments, for at least 90% of a 13.5 month period following the re-treatment, the subject (or population) will have mean improvement score of at least 1.1 or 1.2 to the subject's (or population's) WSRS, or will have a mean WSRS of no more than 2.3 (e.g., no more than 2.2, 2.1, 2, 1.9, 1.8, or 1.7).

In some embodiments, for 100% of a 13.5 month period following the re-treatment, the subject (or population) will have a mean improvement score of at least 1.2 to the subject's WSRS, or will have a mean WSRS of no more than 2.3 (e.g., no more than 2.2, 2.1, 2, 1.9, 1.8, or 1.7). As will be appreciated by one of skill in the art, while the above parameters are described in regard to a 13.5 month period, the improvement can last for longer periods as well. The above discussion simply denotes that for at least the 13.5 months following the re-treatment session, the above aspects will apply. In some embodiments, the subject's (or population's) WSRS will be improved by at least 1.1 for the 13.5 months following the re-treatment session. In some embodiments, the subject's (or population's) WSRS will be at least 1.3, 4.5 months after the re-treatment session. In some embodiments, the subject's (or population's) WSRS will be at least 1.3, 7.5 month after the retreatment session. In some embodiments, the subject's (or population's) WSRS will be at least 1.5, 10.5 months after the re-treatment session. In some embodiments, the subject's (or population's) WSRS will be at least 1.7, 13.5 months after the re-treatment session.

As will be appreciated by one of skill in the art, while the above values and parameters are explicitly described herein in regard to WSRS, corresponding or equivalent values regarding other scales (such as global aesthetic improvement) are also contemplated. For example, in some embodiments, the subject (or population) will have at least a 3.4 mean GAIS throughout the process. In some embodiments, for at least 4.5 of 13.5 months following the re-treatment, the subject (or population) will have at mean GAIS of no less than 3.6, 3.5, 3.4, 3.3, 3.2, 3.1, 3.0, or 2.9. In some embodiments, for at least 3 of 3.5 months following the re-treatment, the subject (or population) will have at mean GAIS of no less than 3.7, 3.6, 3.5, 3.4, 3.3, 3.2, 3.1, 3.0, or 2.9. In some embodiments, for at least 6 of 13.5 months following the re-treatment, the subject (or population) will have at mean GAIS of no less than 3.5, 3.4, 3.3, 3.2, 3.1, 3.0, or 2.9. In some embodiments, for at least 9 of 13.5 months following the retreatment, the subject (or population) will have at mean GAIS of no less than 3.5, 3.4, 3.3, 3.2, 3.1, 3.0, or 2.9. In some embodiments, for 13.5 months following the retreatment, the subject (or population) will have at mean GAIS of no less than 3.4, 3.3, 3.2, 3.1, 3.0, or 2.9. Further optional results and ranges can be found in the examples and tables below. In addition, these values can be generated by the subject and/or the administrator, or a third party, separate from the method. In some embodiments, the magnitude of the result or improvement can be measured at various time points after the re-treatment. In some embodiments, at 4.5 months after the re-treatment, the subject's (or population's) mean WSRS is no more than 2.2 (e.g., less than 2.1, 2, 1.9, 1.8, or 1.7). In some embodiments, at 7.5 months after the re-treatment, the subject's (or population's) mean WSRS is no more than 2.1 (e.g., less than 2, 1.9, 1.8, or 1.7). In some embodiments, at 10.5 months after the re-treatment, the subject's (or population's) mean WSRS is no more than 2 (e.g., less than 1.9, 1.8, or 1.7). In some embodiments, at 13.5 months after the re-treatment, the subject's (or population's) mean WSRS is no more than 1.8 (e.g., less than 1.7).

In some embodiments, at 4.5 months after the re-treatment, the subject's (or population's) mean GAIS is at least 3.5 (e.g., at least 3.5, 3.6, or 3.7). In some embodiments, at 7.5 months after the re-treatment, the subject's (or population's) mean GAIS is at least 3.5 (e.g., at least 3.5, 3.6, or 3.7). In some embodiments, at 10.5 months after the re-treatment, the subject's (or population's) mean GAIS is at least 3.7 (e.g., at least 3.7, 3.8, or 3.9). In some embodiments, at 13.5 months after the re-treatment, the subject's (or population's) mean GAIS is at least 3.7 (e.g., at least 3.7, 3.8, or 3.9).

In some embodiments, the re-treatment method described herein provides surprising and unexpected results by employing less dermal filler for at least the same results as would be expected from two separate, traditional, forms of dermal filler applications. In some embodiments, the re-treatment method described herein provides even more surprising and unexpected results by employing less dermal filler for longer lasting and/or a higher level of improvement to the subject.

In some embodiments, an initial treatment injection (of a single side of a subject) receives 1.1±0.61 mL of a dermal filler, and (optionally) have a touch-up application of 0.5±0.22, within two weeks, bringing the total initial treatment session to 1.6 ml (per half of a subject's face), the amount used in the subsequent session is substantially less than 1.6 ml. In some embodiments, the amount in a re-treatment visit is 0.7±0.33 or 0.7±0.36 (per half of a subject's face), less than half of the 1.6 ml required for the initial treatment. The fact that a second administration of a filler can result in 18 months of total improvement is clearly unexpected, as one would expect that 3.2 ml would be required for 18 months (twice the amount of a single dose). Moreover, prior to the present disclosure, one would have expected that, even if one did administer twice the amount needed for a typical single injection, that at the end of 18 months, the effectiveness of both injections would be substantially diminished or depleted. In contrast, the presently disclosed method can, employing significantly less filler (1.6+0.7=2.3 ml), provide a high level of improvement, even at the very end of the 18 months.

In some embodiments, the amount administered to a subject is twice that disclosed above (as the above numbers are only representative of one-half of a subject's face). In some embodiments, the amount administered in the initial treatment session is between about 0.8 ml and about 2.4 ml (per half of a subject's face). In some embodiments, the amount given in the first injection of the initial treatment session is between about 0.5 ml and about 1.7 ml, for example, 0.5-1.7, 0.6-1.6, 0.7-1.5, 0.8-1.4, 0.9-1.3, 1-1.2, or 1 ml (per half of a subject's face). In some embodiments, the amount provided in an optional touch-up application is between about 0.28 ml and 0.72 ml, for example, 0.28-0.72, 0.3-0.7, 0.4-0.6, or 0.5 ml (per half of a subject's face). In some embodiments, the amount provided for the entire initial treatment session is between about 0.8 ml and 2.4 ml, for example 0.8-2.4, 0.9-2.3, 1-2.2, 1.1-2.1, 1.2-2, 1.3-1.9, 1.4-1.8, 1.5-1.7, or 1.6 ml (for half a subject's face). In some embodiments, the amount of filler provided in the re-treatment session is less than 70% of the amount used in the initial treatment session. For example, in some embodiments, the amount used in the re-treatment session is less than 65, 60, 55, 50, 45, 40, 35, 30, 25, or 20% of the amount used in the initial treatment session, including any range defined between any of the two previous values. In some embodiments, the amount used is between 40% and 50% of the amount used in the initial treatment session, for example 43% or 44%.

In some embodiments, the amount of filler provided in the re-treatment session is less than 90% of the amount used in the first injection of the initial treatment session. For example, in some embodiments, the amount used in the re-treatment session is less than 85, 80, 75, 70, 65, 60, 55, 50, 45, 40, or 35% of the amount used in the first injection of the initial treatment session, including any range defined between any of the two previous values. In some embodiments, the amount used is between 60% and 70% of the amount used in the initial treatment session, for example 63% or 64%.

In some embodiments, the amount of filler provided in the re-treatment session is less than 90% of the amount used in a traditional single injection treatment session. For example, in some embodiments, the amount used in the re-treatment session is less than 85, 80, 75, 70, 65, 60, 55, 50, 45, 40, or 35% of the amount used in a traditional single injection treatment session, including any range defined between any of the two previous values. In some embodiments, the amount used is between 60% and 70% of the amount used in a traditional single injection treatment session, for example 63% or 64%.

In some embodiments, after the initial treatment, the subject can be evaluated during a follow-up session. The follow-up session can be, for example, between one day and two weeks after the initial treatment. In some embodiments, the follow-up session can be two weeks after the initial treatment. In some embodiments, the subject can be evaluated during a series of follow-up sessions ranging from about one day to about 30 months after the initial treatment. In some embodiments, the subject can be evaluated at, for example, about 2 weeks, about 4.5 months, about 9 months, about 12 months, about 15 months, about 18 months, about 24 months, about 27 months and about 30 months after initial treatment.

At each follow-up session, the subject can be evaluated for, for example, aesthetic improvement. Assessment can aid in determining a course of future treatment. In some embodiments, assessment can be done at, for example, the initial treatment visit, two weeks after treatment, and at each subsequent follow-up visit. During visits where treatment is administered, the severity can be rated prior to injection. Aesthetic improvement can be assessed in a variety of ways, including for example, by using a Severity Rating Scale. For example, in some embodiments, a Severity Rating Scale such as the one depicted above can be used to assess the visual appearance of, for example, nasolabial folds.

In some embodiments, each score in the Severity Rating Scale above can be exemplified by, for example, sets of photographs of the area of interest (e.g., nasolabial folds). The above chart provides guidelines for an assessment of wrinkle severity at a certain time-point and is not based on a comparison to the pre-treatment appearance. Similar categorical scales can be developed and used for evaluation of a variety different features and areas of interest.

In some embodiments, the methods disclosed provide a favorable change of at least one score in a Severity Rating Scale. In some embodiments, the methods disclosed provide a favorable change of at least two scores in a Severity Rating Scale.

In various embodiments, aesthetic improvement can also be evaluated for global aesthetic improvement, i.e. improvement from pre-treatment appearance. In some embodiments, the following exemplary categorical scale (in Table 0.2) can be used to measure global aesthetic improvement:

TABLE 0.2

Global Aesthetic Improvement Scale

| Rating | Definition |
| --- | --- |
| Very Much Improved | Optimal cosmetic result for the implant in this subject. |
| Much Improved | Marked improvement in appearance from the initial condition, but not completely optimal for this subject. |
| Improved | Obvious improvement in appearance from the initial condition. |
| No Change | The appearance is essentially the same as baseline. |
| Worse | The appearance is worse than the original condition. |

In some embodiments, point values, scores, or grades can be assigned to the above groups. In some embodiments, the point values, scores, or grades are as follows: 0—Worse; 1—No Change; 2—Improved; 3—Much Improved; and 4—Very Much Improved.

In some embodiments, evaluation can be made in view of the overall cosmetic result for each area of interest. The ratings can be correlated with the actions that would generally be considered in the normal course of practice. Review of a pre-treatment archival photograph (obtained prior to initial treatment) at each follow-up session can aid in the assessment. In some embodiments, the methods disclosed provide a favorable change of at least one step in a Global Aesthetic Improvement Scale. In some embodiments, the methods disclosed provide a favorable change of at least two steps in a Global Aesthetic Improvement Scale. In some embodiments, the methods disclosed provide a favorable change of at least three steps in a Global Aesthetic Improvement Scale.

In some embodiments, the assessment is performed at, for example, about two weeks after treatments and at each subsequent visit.

In various embodiments, photography can be used to aid in evaluation of treatment. Photographs can be taken prior to initial treatment. Such photographs can serve as reference for post-treatment assessment of Global Aesthetic Improvement. In some embodiments, the set of photographs can include at least one direct frontal view centered on the subject's face (i.e., both nasolabial folds are clearly visible). In various embodiments, archival photographs can be taken at follow-up sessions to, for example, document treatment result. In some embodiments, the photography can be done in accordance with, for example, the standard Canfield system.

In some embodiments, touch-up of a treatment can be performed. Areas of treatment can be touched-up during, for example, a follow-up session. In various embodiments, the touch-up of a previous treatment is performed. Touch-up can be performed, for example, after an initial treatment or after re-treatment. In some embodiments, touch-up can be distinguished from a treatment or re-treatment because a touch-up occurs within two weeks of a treatment or re-treatment. In some embodiments, a "touch-up" follows an initial treatment session to build upon the adjustments in the previous session in order to obtain a full correction. In some embodiments, a "touch-up" is defined as involving less than 0.5 ml of dermal filler. In some embodiments, the touch-up is defined as a combination or all of the above.

In some embodiments, scheduling of a subsequent treatment can be arranged based on the timing of a touch-up application. In some embodiments, a re-treatment can be scheduled between about 4 and about 10 months after a touch-up application. In some embodiments, a re-treatment can be scheduled for about 1-2, 2-2.5, 2.5-3, 3-3.5, 3.5-4, 4-4.5, 4.5-5, 5-5.5, 5.5-6, 6-6.5, 6.5-7, 7-7.5, 7.5-8, 8-8.5, 8.5-9, 9-9.5, 9.5-10, 10-10.5, 10.5-11, 11-11.5, 11.5-12, or more months after a touch-up application.

In some embodiments, the disclosed methods can result in a prolonging of treatment results for more than 18 months after initial treatment. In some embodiments, earlier re-treatment, such as, for example, re-treatment at between about 2 months and about 9 months after an initial treatment session, can provide increased maintenance of treatment results. The increased maintenance of treatment results can be without significant decrease in volume during the treatment period. For example, little or no loss of volume can be observed for up to about 18 months after initial treatment. In some embodiments in which a subject is re-treated within five months of an initial treatment, no significant decrease in volume is experienced for a period of at least about 18 months after initial treatment. In some embodiments, re-treatment results in maintenance of treatment results at a severity rating without an increase in the severity rating for at least about 18 months after initial treatment. In some embodiments, the severity rating is maintained at mild for at least about 12 months after initial treatment.

In some embodiments, the use of an initial treatment and correctly timed re-treatment can be used to extend the effective lifetime of the initial full correction. In some embodiments, the improvement score that is obtained from the initial treatment can be maintained for at least a year following the re-treatment session (see, e.g., FIG. 4).

In some embodiments, as can be observed in FIG. 4, a relatively early re-treatment session provides the benefit of the earlier re-treatment (maintaining a higher level of improvement score throughout a treatment period), while also providing for the extended duration of effectiveness of the re-treatment (e.g., over a year of maintained improvement). Thus, some embodiments are especially advantageous as they not only provide for an extended duration of maintained improvement, but the method can also help maintain a heightened level of improvement during that period. Thus, in some embodiments, the re-treatment session is administered before 9 months (following the initial treatment) and can be, for example 8-7, 7-6, 6-5, 5-4, 4-3, 3-2 months or less following the re-treatment. As will be appreciated by one of skill in the art, in light of the present disclosure, enough time should pass after the initial treatment to allow for some of the filler from the initial treatment to be absorbed, allowing space for additional injectable filler to be added.

In some embodiments, the application of an initial treatment followed by a re-treatment can be used to stimulate an increase in collagen production. In particular, in some embodiments, timely administered re-treatments will provide for an increase in improvement score over several months after the re-treatment session, without requiring the additional injection of the injectable filler.

In various embodiments, the disclosed methods can provide improvement in volume and/or firmness. The improvement in volume and/or firmness can occur, for example, gradually over a period of time. In some embodiments, the improvement can occur over a period of about one day to about 18 months.

In some embodiments, the improvement can be, for example, a favorable change of at least one score on a severity rating scale. In some embodiments, the improvement can be, for example, a change in severity rating from moderate to mild. In some embodiments, the improvement can be, for example, a change in severity rating from mild to absent. In some embodiments, the improvement can be measured by a favorable change in global aesthetic rating. For example, the improvement can be a favorable change of at least one step on a global aesthetic rating scale. In some embodiments, the improvement can be, for example, a change in rating from improved to much improved. In some embodiments, the improvement can be, for example, a change in rating from much improved to very much improved. In some embodiments, the improvement can be, for example, a change in rating from improved to very much improved.

In some embodiments, screening evaluations can be conducted prior to treatment. The screening evaluations can include, for example, medical history (including any prior dermatological procedures or implants), physical examination, including vital signs, medication history, pregnancy test, and obtaining informed consent. In some embodiments, women of childbearing potential can have a urine pregnancy test before treatment. Before the treatment, the subject's need for pain relief can be assessed. Local or topical anaesthetics or a dental block can be used, if needed.

In some embodiments, the injectable filler can be, for example, sterile, viscoelastic and, free from products of animal origin. In various embodiments, the injectable filler can be packaged in, for example, sterile syringes and supplied with a sterilized needle. The product can be dispersed in, for example, a physiological saline solution about pH 7.

In various embodiments, the treatment site can be cleaned with a suitable antiseptic solution. The injectable filler can be administered using, for example, a thin gauge needle by injecting the material into, for example, the deep dermis and/or the surface layer of subcutis. In some embodiments, if the injectable filler is injected too deep or intramuscularly, the duration of the implant may be shorter because of a higher filler turnover rate. In some embodiments, too superficial an injection may give blanching effects and bumps on the treatment site. Before injecting, the air may be removed from the syringe up to the point where a droplet is visible on top of the needle.

The injection technique with regard to the depth of injection and the administered quantity can vary. A variety of injection techniques are known in the art and can be used in conjunction with the embodiments described herein. In various embodiments, the linear threading technique can be used to carefully lift up a wrinkle or fold. In other embodiments, a series of punctual injections or a combination of the two techniques can be used. In some embodiments, the eye of the needle preferable faces upwards during injection. In some embodiments, the contour of the needle can preferably be visible. In some embodiments, the injectable filler is injected while pulling the needle slowly backwards. Injection can stop just before the needle is pulled out from the skin to prevent material from leaking out from the injection site.

In some embodiments, concomitant medications or other treatments may be utilized when medically necessary. Concomitant medications, may include, for example, over-the-counter (OTC) medications, and procedures such as, for example, surgery/biopsy or diagnostic evaluations.

In some embodiments, the methods and systems disclosed herein allow for improved efficacy of injectable filler compositions. More particularly, some of the embodiments disclosed herein provide methods and systems that prolong the efficacy of injectable fillers for periods of at least about 18 months after initial treatment. Some of the embodiments herein provide methods and systems that provide continuous improvement in volume and/or firmness in a subject. Thus, in some of the embodiments, the methods and systems disclosed herein provide increased aesthetic benefit by prolonging the results of injectable fillers and providing for a continued decrease in wrinkle severity.

While not intending to be limited by theory, it is believed that, in some embodiments, by performing a first and then a second treatment session, with the correct interval between the two, one can enhance the effectiveness of the later dermal filler injection session (the re-treatment). Without intending to be limited by theory, it is hypothesized that the initial treatment, can aid by maintaining expansile tension and slow the rate of resorbtion following the re-treatment. In some embodiments, the long lasting effect reported here can be amplified by injection-stimulated collagen production and collagen breakdown inhibition that outlasts the filling of space by the injected gel As will be appreciated by one of skill in the art, in light of the present disclosure, there are a number of issues or effects that are common in prior administration techniques. Various embodiments described herein can address some or all of these issues. Previous techniques had a tendency to be limited to short-term results. For example, traditional techniques may result in loss of volume and/or firmness over time. Loss of volume and/or firmness may be caused by, for example, resorbtion of injectable filler composition. With traditional techniques, product volume in superficial tissues may be over filled to obtain longer lasting results, which may not be aesthetically pleasing. In addition, traditional techniques tended to show an increase in severity rating over time. Additionally, traditional techniques did not provide for continued improvement. As will be appreciated by one of skill in the art, not all of the disclosed embodiments need address any, some, or all of the above noted issues.

In some embodiments, the methods described herein can further include a step of identifying a subject to apply the method to. In some embodiments, this involves identifying a subject that should or would benefit from receiving at least 10 months of improved volume and/or firmness (which can be measured on the WSRS or GAIS in some embodiments). In some embodiments, the step involves identifying a subject that should or would benefit from a continuing increase in volume and/or firmness (which can be measured on the WSRS or GAIS in some embodiments) over a period following a re-treatment and continuing for at least 9, 10, 11, 12, 13, or more months.

In some embodiments, methods and systems disclosed herein provide for ease of training or instruction for improving the efficacy of an injectable filler. As is appreciated by one of skill in the art, in some situations, it can be difficult to obtain long-term results using conventional administration methods. Additionally, as will be appreciated by one of skill in the art, to some extent, the application of dermal fillers in the cosmetics industry can be characterized as more of an "art" than a science. In other words, training people in this process can often be a trial and error experience rather than involving a clear set of instructions and signposts to follow.

Thus, in some embodiments, provided herein are systems and methods that can be, relatively speaking, readily and/or clearly taught. In some embodiments, this involves teaching others how to perform the treatment methods described herein. In some embodiments, the re-treatment method lends itself to ready communication to others and discussion of how and why the technique works. Additionally, in some embodiments, the technique can be readily applied by numerous and different people with different backgrounds. That is, in some embodiments, the teaching of the above treatment methods provides for increased reproducibility of the results described herein with the relevant products. In some of the embodiments, providing users with the knowledge of these methods provides quality control for improving the efficacy of a filler composition. Thus, in some embodiments, a method for teaching a technique that is especially amenable to teaching (and/or the other aspects noted above) is provided. In some embodiments, the teaching of the method itself also provides the above noted advantages of providing users with a basic technique in common, reproducibility and predictability of results, and allowing a broader range of people to apply the filler. Of course, the application of the technique itself can have the specific advantages noted herein as well.

In some embodiments, a kit for improving the efficacy of an injectable filler is provided. The kit can include a dermal filler, a syringe, a needle, and instructions or guidance for performing parts of or all of some or all of the above techniques. In some embodiments, the dermal filler is RESTYLANE® or PERLANE® dermal filler. The instructions can be provided on a variety of formats, such as electronic (data file, DVD, downloadable, etc) or pamphlets. The syringe can be a 2 ml or smaller syringe. In some embodiments, the syringe is prefilled with the dermal filler. In some embodiments, the kit comprises a first plurality of syringes, wherein each of the first plurality of syringes has a first volume. In some embodiments, the first volume is between 1 and 5 ml, e.g., 1, 2, 3, 4, or 5. In some embodiments, the kit comprises a second plurality of syringes, wherein each of the second plurality of syringes has a second volume and wherein the second volume is approximately one half of the first volume. In some embodiments, the second volume is between 0.5 and 2.5 ml, e.g., 0.5, 1, 1.5, 2, or 2.5. In some embodiments, the second volume is approximately 70% of the first volume.

In some embodiments, the kit includes gloves. In some embodiments, the kit includes sterilizing material. In some embodiments the kit includes a cloth or other absorbent material.

In some embodiments, the kit includes software for assisting in capturing images of the subject's face. In some embodiments, the software compares two facial images of the subject and determines where one should inject and/or re-inject the dermal filler by identifying the areas that appear to lack volume or appear to have lost volume. In some embodiments, the software compares two facial images of the subject and assesses improvement or worsening of wrinkle severity.

In some embodiments, a training kit is provided. The kit can include instructions or guidance for performing parts of or all of some or all of the above techniques. The instructions can be provided on a variety of formats, such as electronic (data file, DVD, downloadable, etc) or pamphlets. The instructions can generally provide one with any of the steps outlined herein. For example, the instructions can include information regarding how much to inject, how to touch-up after an injection, the amount of time to wait before re-treatment, the amount of time it may take for a procedure and for patient recovery after the procedure, the amount of pain that occurs during the procedure, advantages of the re-treatment technique over standard techniques, the results that can be expected, and how the injections should be made in particular situations. In some embodiments, the training kit includes before and after depictions of subjects that have received the treatment.

As will be appreciated by one of skill in the art, in some embodiments, the training kit not only provides training for the user of the technique, but can also provide additional information to help the user sell the technique to potential clients. In some embodiments, the kit includes information to help the user order additional dermal filler.

EXAMPLES

Example 1

Methods for Prolonging Dermal Filler Effect

This example illustrates a treatment protocol for maintaining injectable filler efficacy at least as long as one year after re-treatment.

In this example, a subject that desires added volume or firmness is treated with injectable filler. Touch-up with injectable filler can optionally be done within one to two weeks of the initial treatment. At 4½ months after the initial treatment, the subject is re-treated with injectable filler. One can assess differences in visual severity of the treatment area, for example, utilizing the 5-point scale Wrinkle Severity Rating Score (WSRS), at, for example, the initial visit, week two, 4½ months (before re-treatment), 9 months, 12 months, 15 months and 18 months. Re-treatment provides prolonged maintenance of treatment results. Aesthetic improvement can also be observed.

Example 2

Persistence of RESTYLANE® Dermal Filler Effect

This example illustrates generally a study involving a treatment protocol to prolong RESTYLANE® dermal filler efficacy at least as long as one year after re-treatment.

The objective of the study outlined in this example was to evaluate the efficacy of RESTYLANE® dermal filler for the correction of nasolabial folds (NLF) and the effect of different re-treatment schedules to affect the persistence of a cosmetic improvement. Study findings demonstrated a duration of effect with RESTYLANE® dermal filler resulting from 4½ and 9 month re-treatment sessions (85 percent and 88 percent, respectively). Furthermore, with a re-treatment at 9 months, 97 percent of subjects maintained response at 18 months.

75 subjects were evaluated to test the effect of two different re-treatment schedules, in a split-face design. Each subject had both nasolabial folds corrected with RESTYLANE® dermal filler, one side of the face was randomly selected to be corrected with RESTYLANE® dermal filler and then re-treated at 4½ months, and the opposite side was re-treated at 9 months. Subjects were followed in the interim, and both NLFs were re-treated at 18 months.

Blinding was accomplished by utilizing one medically qualified individual to administer the treatments and an evaluating investigator (who was blinded to the randomization) to conduct the NLF evaluations. The study measured differences in visual severity of the nasolabial folds, utilizing the 5-point scale Wrinkle Severity Rating Score (WSRS), as assessed by the evaluating investigator at initial visit, week two, 4½ months (before re-treatment), 9 months (before re-treatment), 12 months, 15 months and 18 months. A responder was defined as anyone who had achieved at least a one grade improvement in WSRS at any time point.

This study enrolled a total of 75 subjects with a mean population age of 53.8 years (range 26-73). Subjects were excluded from the study if they had undergone procedures based on active dermal response (e.g., laser and chemical peeling procedure) within 6 months prior to study start or if they had any facial tissue augmenting therapy or aesthetic facial surgery within 9 months prior to study start. Study participants were predominantly Caucasian female, and only 8 percent of those enrolled had undergone prior augmentation therapy. Mean baseline WSRS was 3.2 (0-4 scale) in the NLF, and there was no statistical difference in WSRS between the side re-treated at 4½ months and the side re-treated at 9 months.

After the initial and touch-up injections, 93 percent of subjects had treatment success. At the 4½ month visit, 85 percent of subjects still maintained treatment success prior to the re-treatment of that NLF. At the 9 month visit, 88 percent of subjects maintained treatment success prior to re-treatment of the other NLF. At the last 18 months evaluation point, 97 percent of subjects had maintained treatment success prior to receiving their last injection of RESTYLANE® dermal filler.

An Area Under the Curve analysis reveals that subjects maintained a better appearance overall in the earlier re-treatment schedule compared to the later re-treatment schedule.

Subjects in this study received an average 3.92 ml (total) of RESTYLANE® dermal filler during the 18 month study period (not including any 18 month re-treatment). There is no statistical difference in volume due to these two re-treatment schedules.

Example 3

Study Design for Comparing Re-Treatment at Different Timepoints

This example illustrates one possible design of a study for comparing re-treatment at different time points. As will be appreciated by one of skill in the art, the study can be repeated to examine various durations, injectable fillers, and other variables.

The objective of this example is to evaluate the efficacy of injectable fillers for the correction of nasolabial folds and the effect of the re-treatment schedule on the overall persistence of the implant. The primary objective is to evaluate the duration of efficacy of injectable fillers, after multiple treatments and at different time points, in regards to differences in visual severity of the nasolabial folds, as assessed by, for example, the Evaluating Investigator at different time points. The primary endpoint can be, for example, the scores in the Severity Rating Scale, obtained at visits. A secondary objective of the study in this example can include, for example: severity of the wrinkles at other time-points during the study and as assessed by the subject, and Global Aesthetic Improvement as judged by the Evaluating Investigator and the subject.

Subjects frequently seek correction of facial contour deformities (age- or disease-related). Wrinkles, folds, scars, and other depressed lesions are often treated with surgery or implantation. In these cases, correction of the depression can be the goal of therapy.

In the conduct of a controlled clinical trial, it is important to assure that both treatment groups have the same degree of abnormality at baseline. While a wide variety of contour deformities could potentially be corrected using a biodegradable implant (e.g., traumatic scars, acne scars, glabellar lines, nasolabial folds), it can be difficult to match two parallel treatment groups for the size and location of acne scars. As a result, it is desirable to choose a bilateral (and approximately symmetrical) lesion for study in a randomized, controlled trial. In the case of a biodegradable implant, an additional selection criterion for the target lesion is the ability of the model to demonstrate the initial treatment effect and to monitor the duration of the effect. Since there are a variety of agents which can obtain a satisfactory initial degree of correction, the key issue with a biodegradable implant is its duration of effect.

Nasolabial folds are fairly large, bilateral fissures that can be augmented and assessed with relative ease. Augmentation to fill the groove is the clear goal of treatment. Each subject can serve as their own control by randomly assigning the test and control treatment to contralateral sides of the face (although these lesions can not be the exactly same size, they can be close and the randomization procedure can reasonably be expected to balance size across the study population). This type of trial can also balance the randomization for skin type or other factors that might affect the outcome. In addition, it has been demonstrated that trials of reasonable duration (6-12 months) can reliably detect the loss of augmentation (or degree of correction) associated with biodegradable implants. Gormley et al., *J Dermatol Surg Oncol* 1990; 16(12):1147-1151, incorporated herein in its entirety.

The administration of injectable filler using similar injection techniques and volumes but different re-treatment schedules is planned. It is desirable to use a volume enough to give 100% correction of the folds at each treatment. The results of this comparison, with respect to the efficacy profiles as well as the persistence of treatment and re-treatment, would be beneficial to both the end user and the subject. The purpose of adding a third re-treatment at month 18 is to test if multiple treatments of injectable filler can give longer longevity of the cosmetic result for subjects.

The evaluation of biodegradable implants involves the assessment of "short-term" and "long-term" responses. Short-term responses can include the initial degree of correction, adverse events associated with the injection of the implant (e.g., pain, swelling, erythema, bruising, or itching), and the time course for resolution of any injection-related adverse events. Based on clinical experience, the majority of short-term injection-related adverse events would be expected to develop quickly and resolve within a few days of the implantation procedure. Long-term responses can include any late-developing adverse events and persistence of the implant. With respect to the overall efficacy of a biodegradable implant it would appear that the most important issue is the duration of effect. This is dependent on the product's inherent rate of bio-degradation, individual subject differences, and the location of the implant. The current study design (randomization of nasolabial folds within individual study participants to the test and control implant) should help control for differences related to subject variability and location of the implant while testing for the effect of re-treatment schedule.

The study can employ a randomized, evaluator-blind design and follow the protocol outlined in FIG. 1. One of the nasolabial folds can be randomly assigned to be corrected with injectable filler and then re-treated at 4½ months. The opposite side can be treated with injectable filler and not re-treated until 9 months. Both nasolabial folds can then be re-treated at 18 months. Each subject can serve as their own control, allowing comparison of the outcome between the contralateral sides. Blinding can be accomplished by utilizing one qualified individual to administer the treatments and a second medically qualified individual (who is blinded to the randomization) to conduct the direct evaluations. The subjects can be aware that they are receiving both treatment schedules.

Example 4

Multi-Center U.S. Trial

The present example was carried out (regardless of the tense used in the example) in a clinical setting (and thus some natural variation from the general description of the example is to be expected as a practical matter). In order to evaluate nonanimal stabilized hyaluronic acid 100,000 gel particles/ml filler's efficacy and persistence for correcting nasolabial folds using 2 re-treatment schedules, a randomized, evaluator-blind design study compared a nasolabial fold corrected with NASHA gel filler (as an initial treatment) and 1) re-treated at 4.5 months with 2) the contralateral fold retreated at 9 months. Participants (n=75) served as their own controls. Touch-up treatments were given to 44 participants 2 weeks post-initial treatment. Folds were rated from 2 weeks to 18 months after the first treatment. The details of this study are provided below and are followed by a summary of the results.

Detailed Description of Study

This example illustrates the results of a multi-center U.S. trial for comparing re-treatment at different time points. The trial involved enrolment of approximately 75 subjects at three centers. Study results are provided, in the following Tables 4.1-4.4 below. In regard to Tables 4.1-4.4, Treatment Schedule A involved the right side being re-treated with Restylane at 4½ months (left side untreated at 4½ months) and the left side being re-treated with Restylane at 9 months (right side untreated at 9 months). Treatment Schedule B involved the left side re-treated with Restylane at 4½ months (right side untreated at 4½ months) and the right side being re-treated with Restylane at 9 months (left side untreated at 9 months). The P-value was from a nonparametric Wilcoxon signed rank sum test.

TABLE 4.1

Restylane Resorbption Rate Over Time
Evaluator's Wrinkle Severity Rating Score (WSRS)
(Intent to Treat Population)

| Visit | WSRS | Side Re-Treated 4½ months (N = 75) | Side Re-Treated 9 months (N = 75) | P-Value |
|---|---|---|---|---|
| Screening (Day 0) | Evaluator WSRS n (%) | | | |
| | Absent | 0 | 0 | |
| | Mild | 1 (1) | 0 | |
| | Moderate | 45 (60) | 46 (61) | |
| | Severe | 25 (33) | 25 (33) | |
| | Extreme | 4 (5) | 4 (5) | |

TABLE 4.1-continued

Restylane Resorbption Rate Over Time
Evaluator's Wrinkle Severity Rating Score (WSRS)
(Intent to Treat Population)

| Visit | WSRS | Side Re-Treated 4½ months (N = 75) | Side Re-Treated 9 months (N = 75) | P-Value |
|---|---|---|---|---|
| | WSRS at re-tx 9 months side - re-tx 4½ months side n (%) | | | 1.000 |
| | −1 | 6 (8) | | |
| | 0 | 62 (83) | | |
| | 1 | 7 (9) | | |
| Visit T (Touch-up) | Evaluator WSRS n (%) | | | |
| | Absent | 1 (2) | 2 (5) | |
| | Mild | 16 (36) | 13 (30) | |
| | Moderate | 21 (48) | 23 (52) | |
| | Severe | 6 (14) | 6 (14) | |
| | Extreme | 0 | 0 | |
| | WSRS at re-tx 9 months side - re-tx 4½ months side n (%) | | | 1.000 |
| | −1 | 2 (5) | | |
| | 0 | 39 (89) | | |
| | 1 | 3 (7) | | |
| Visit 2 (2 weeks) | Evaluator WSRS n (%) | | | |
| | Absent | 35 (49) | 30 (42) | |
| | Mild | 23 (32) | 30 (42) | |
| | Moderate | 13 (18) | 11 (15) | |
| | Severe | 1 (1) | 0 | |
| | Extreme | 0 | 0 | |
| | WSRS at re-tx 9 months side - re-tx 4½ months side n (%) | | | 1.000 |
| | −1 | 9 (13) | | |
| | 0 | 53 (75) | | |
| | 1 | 9 (13) | | |
| Visit 3 (4½ months) (before re-treatment) | Evaluator WSRS n (%) | | | |
| | Absent | 11 (16) | 14 (21) | |
| | Mild | 32 (47) | 25 (37) | |
| | Moderate | 21 (31) | 23 (34) | |
| | Severe | 4 (6) | 6 (9) | |
| | Extreme | 0 | 0 | |
| | WSRS at re-tx 9 months side - re-tx 4½ months side n (%) | | | |
| | −1 | 9 (13) | | 0.526 |
| | 0 | 47 (69) | | |
| | 1 | 12 (18) | | |
| Visit 4 (9 months) (before re-treatment) | Evaluator WSRS n (%) | | | |
| | Absent | 16 (25) | 8 (12) | |
| | Mild | 26 (40) | 33 (51) | |
| | Moderate | 21 (32) | 20 (31) | |
| | Severe | 2 (3) | 2 (3) | |
| | Extreme | 0 | 2 (3) | |
| | WSRS at re-tx 9 months side - re-tx 4½ months side n (%) | | | |
| | −1 | 8 (12) | | 0.013 |
| | 0 | 36 (55) | | |
| | 1 | 21 (32) | | |
| Visit 5 (12 months) | Evaluator WSRS n (%) | | | |
| | Absent | 10 (16) | 10 (16) | |
| | Mild | 39 (62) | 39 (62) | |
| | Moderate | 13 (21) | 9 (14) | |
| | Severe | 1 (2) | 5 (8) | |
| | Extreme | 0 | 0 | |
| | WSRS at re-tx 9 months side - re-tx 4½ months side n (%) | | | |
| | −1 | 7 (11) | | 0.481 |
| | 0 | 45 (71) | | |
| | 1 | 11 (17) | | |
| Visit 6 (15 months) | Evaluator WSRS n (%) | | | |
| | Absent | 18 (28) | 14 (22) | |
| | Mild | 31 (48) | 36 (56) | |
| | Moderate | 15 (23) | 12 (19) | |
| | Severe | 0 | 2 (3) | |
| | Extreme | 0 | 0 | |
| | WSRS at re-tx 9 months side - re-tx 4½ months side n (%) | | | |
| | −2 | 1 (2) | | 0.386 |
| | −1 | 5 (8) | | |
| | 0 | 46 (72) | | |
| | 1 | 12 (19) | | |

TABLE 4.1-continued

Restylane Resorbption Rate Over Time
Evaluator's Wrinkle Severity Rating Score (WSRS)
(Intent to Treat Population)

| Visit | WSRS | Side Re-Treated 4½ months (N = 75) | Side Re-Treated 9 months (N = 75) | P-Value |
|---|---|---|---|---|
| Visit 7 (18 months) (before re-treatment) | Evaluator WSRS n (%) | | | |
| | Absent | 21 (33) | 21 (33) | |
| | Mild | 34 (54) | 31 (49) | |
| | Moderate | 8 (13) | 11 (17) | |
| | Severe | 0 | 0 | |
| | Extreme | 0 | 0 | |
| | WSRS at re-tx 9 months side - re-tx 4½ months side n (%) | | | |
| | −1 | 8 (13) | | 0.648 |
| | 0 | 44 (70) | | |
| | 1 | 11 (17) | | |

TABLE 4.2

Restylane Resorbption Rate Over Time
Subject's Wrinkle Severity Rating Score (WSRS)
(Intent to Treat Population)

| Visit | WSRS | Side Re-Treated 4½ months (N = 75) | Side Re-Treated 9 months (N = 75) | P-Value |
|---|---|---|---|---|
| Screening (Day 0) | Evaluator WSRS n (%) | | | |
| | Absent | 0 | 0 | |
| | Mild | 5 (7) | 1 (1) | |
| | Moderate | 47 (63) | 52 (69) | |
| | Severe | 21 (28) | 18 (24) | |
| | Extreme | 2 (3) | 4 (5) | |
| | WSRS at re-tx 9 months side - re-tx 4½ months side n (%) | | | |
| | −1 | 5 (7) | | 0.302 |
| | 0 | 60 (80) | | |
| | 1 | 10 (13) | | |
| Visit T (Touch-up) | Subject WSRS n (%) | | | |
| | Absent | 1 (2) | 3 (7) | |
| | Mild | 13 (30) | 9 (20) | |
| | Moderate | 30 (68) | 32 (73) | |
| | Severe | 0 | 0 | |
| | Extreme | 0 | 0 | |
| | WSRS at re-tx 9 months side - re-tx 4½ months side n (%) | | | |
| | −1 | 5 (11) | | 1.000 |
| | 0 | 34 (77) | | |
| | 1 | 5 (11) | | |
| Visit 2 (2 weeks) | Subject WSRS n (%) | | | |
| | Absent | 14 (19) | 15 (21) | |
| | Mild | 39 (54) | 37 (52) | |
| | Moderate | 19 (26) | 17 (24) | |
| | Severe | 0 | 2 (3) | |
| | Extreme | 0 | 0 | |
| | WSRS at re-tx 9 months side - re-tx 4½ months side n (%) | | | |
| | −1 | 7 (10) | | 1.000 |
| | 0 | 56 (79) | | |
| | 1 | 8 (11) | | |
| Visit 3 (4½ months) (before re-treatment) | Subject WSRS n (%) | | | |
| | Absent | 7 (10) | 9 (13) | |
| | Mild | 27 (40) | 21 (31) | |
| | Moderate | 32 (47) | 35 (51) | |
| | Severe | 2 (3) | 3 (4) | |
| | Extreme | 0 | 0 | |
| | WSRS at re-tx 9 months side - re-tx 4½ months side n (%) | | | |
| | −1 | 9 (13) | | 0.680 |
| | 0 | 48 (71) | | |
| | 1 | 10 (15) | | |
| | 2 | 1 (1) | | |

TABLE 4.2-continued

Restylane Resorbption Rate Over Time
Subject's Wrinkle Severity Rating Score (WSRS)
(Intent to Treat Population)

| Visit | WSRS | Side Re-Treated 4½ months (N = 75) | Side Re-Treated 9 months (N = 75) | P-Value |
|---|---|---|---|---|
| Visit 4 (9 months) (before re-treatment) | Subject WSRS n (%) | | | |
| | Absent | 11 (17) | 6 (9) | |
| | Mild | 34 (52) | 26 (40) | |
| | Moderate | 18 (28) | 32 (49) | |
| | Severe | 2 (3) | 1 (2) | |
| | Extreme | 0 | 0 | |
| | WSRS at re-tx 9 months side - re-tx 4½ months side n (%) | | | |
| | −1 | 6 (9) | | 0.001 |
| | 0 | 37 (57) | | |
| | 1 | 21 (32) | | |
| | 2 | 1 (2) | | |
| Visit 5 (12 months) | Subject WSRS n (%) | | | |
| | Absent | 9 (14) | 12 (19) | |
| | Mild | 37 (58) | 38 (59) | |
| | Moderate | 16 (25) | 12 (19) | |
| | Severe | 2 (3) | 2 (3) | |
| | Extreme | 0 | 0 | |
| | WSRS at re-tx 9 months side - re-tx 4½ months side n (%) | | | |
| | −1 | 13 (20) | | 0.167 |
| | 0 | 45 (70) | | |
| | 1 | 6 (9) | | |
| Visit 6 (15 months) | Subject WSRS n (%) | | | |
| | Absent | 2 (3) | 6 (9) | |
| | Mild | 40 (63) | 31 (48) | |
| | Moderate | 19 (30) | 23 (36) | |
| | Severe | 3 (5) | 4 (6) | |
| | Extreme | 0 | 0 | |
| | WSRS at re-tx 9 months side - re-tx 4½ months side n (%) | | | |
| | −1 | 9 (14) | | 0.824 |
| | 0 | 44 (69) | | |
| | 1 | 11 (17) | | |
| Visit 7 (18 months) (before re-treatment) | Subject WSRS n (%) | | | |
| | Absent | 5 (8) | 8 (13) | |
| | Mild | 39 (62) | 31 (49) | |
| | Moderate | 17 (27) | 23 (37) | |
| | Severe | 1 (2) | 1 (2) | |
| | Extreme | 1 (2) | 0 | |
| | WSRS at re-tx 9 months side - re-tx 4½ months side n (%) | | | |
| | −2 | 1 (2) | | 1.000 |
| | −1 | 10 (16) | | |
| | 0 | 40 (63) | | |
| | 1 | 12 (19) | | |

TABLE 4.3

Restylane Resorbption Rate Over Time
Evaluator's Global Aesthetic Improvement (GAI)
(Intent to Treat Population)

| Visit | GAI | Side Re-Treated 4½ months (N = 75) | Side Re-Treated 9 months (N = 75) | P-Value |
|---|---|---|---|---|
| Visit T (Touch-up) | Evaluator GAI n (%) | | | |
| | Worse | 0 | 0 | |
| | No Change | 1 (2) | 1 (2) | |
| | Improved | 25 (57) | 24 (55) | |
| | Much Improved | 17 (39) | 18 (41) | |
| | Very Much Improved | 1 (2) | 1 (2) | |
| | GAI at 9 months-4½ months n (%) | | | |
| | 0 | 43 (98) | | 1.000 |
| | 1 | 1 (2) | | |
| Visit 2 (2 weeks) | Evaluator GAI n (%) | | | |
| | Worse | 0 | 0 | |
| | No Change | 0 | 0 | |
| | Improved | 2 (3) | 2 (3) | |

TABLE 4.3-continued

Restylane Resorbption Rate Over Time
Evaluator's Global Aesthetic Improvement (GAI)
(Intent to Treat Population)

| Visit | GAI | Side Re-Treated 4½ months (N = 75) | Side Re-Treated 9 months (N = 75) | P-Value |
|---|---|---|---|---|
| | Much Improved | 24 (33) | 24 (34) | |
| | Very Much Improved | 46 (64) | 45 (63) | |
| | GAI at 9 months-4½ months n (%) | | | |
| | −1 | 1 (1) | | 1.000 |
| | 0 | 70 (99) | | |
| Visit 3 (4½ months) (before re-treatment) | Evaluator GAI n (%) | | | |
| | Worse | 0 | 0 | |
| | No Change | 0 | 1 (1) | |
| | Improved | 6 (9) | 6 (9) | |
| | Much Improved | 29 (43) | 27 (40) | |
| | Very Much Improved | 33 (49) | 34 (50) | |
| | GAI at 9 months-4½ months n (%) | | | |
| | −2 | 1 (1) | | 1.000 |
| | −1 | 2 (3) | | |
| | 0 | 62 (91) | | |
| | 1 | 3 (4) | | |
| Visit 4 (9 months) (before re-treatment) | Evaluator GAI n (%) | | | |
| | Worse | 0 | 0 | |
| | No Change | 1 (2) | 1 (2) | |
| | Improved | 4 (6) | 5 (8) | |
| | Much Improved | 22 (34) | 23 (35) | |
| | Very Much Improved | 38 (58) | 36 (55) | |
| | GAI at 9 months-4½ months n (%) | | | |
| | −1 | 5 (8) | | 0.453 |
| | 0 | 58 (89) | | |
| | 1 | 2 (3) | | |
| Visit 5 (12 months) | Evaluator GAI n (%) | | | |
| | Worse | 0 | 0 | |
| | No Change | 0 | 0 | |
| | Improved | 4 (6) | 4 (6) | |
| | Much Improved | 24 (38) | 21 (33) | |
| | Very Much Improved | 36 (56) | 39 (61) | |
| | GAI at 9 months-4½ months n (%) | | | |
| | −1 | 3 (5) | | 0.508 |
| | 0 | 55 (86) | | |
| | 1 | 6 (9) | | |
| Visit 6 (15 months) | Evaluator GAI n (%) | | | |
| | Worse | 0 | 0 | |
| | No Change | 0 | 0 | |
| | Improved | 1 (2) | 1 (2) | |
| | Much Improved | 17 (27) | 23 (36) | |
| | Very Much Improved | 46 (72) | 40 (63) | |
| | GAI at 9 months-4½ months n (%) | | | |
| | −1 | 9 (14) | | 0.183 |
| | 0 | 53 (83) | | |
| | 1 | 1 (2) | | |
| | 2 | 1 (2) | | |
| Visit 7 (18 months) (before re-treatment) | Evaluator GAI n (%) | | | |
| | Worse | 0 | 0 | |
| | No Change | 0 | 1 (2) | |
| | Improved | 2 (3) | 1 (2) | |
| | Much Improved | 17 (27) | 11 (17) | |
| | Very Much Improved | 44 (70) | 50 (79) | |
| | GAI at 9 months-4½ months n (%) | | | |
| | −1 | 2 (3) | | 0.180 |
| | 0 | 54 (86) | | |
| | 1 | 7 (11) | | |

TABLE 4.4

Restylane Resorbption Rate Over Time
Subject's Global Aesthetic Improvement (GAI)
(Intent to Treat Population)

| Visit | GAI | Side Re-Treated 4½ months (N = 75) | Side Re-Treated 9 months (N = 75) | P-Value |
|---|---|---|---|---|
| Visit T (Touch-up) | Subject GAI n (%) | | | |
| | Worse | 0 | 0 | |
| | No Change | 2 (5) | 2 (5) | |
| | Improved | 25 (57) | 26 (59) | |
| | Much Improved | 13 (30) | 12 (27) | |
| | Very Much Improved | 4 (9) | 4 (9) | |
| | GAI at 9 months-4½ months n (%) | | | |
| | −1 | 4 (9) | | 1.000 |
| | 0 | 37 (84) | | |
| | 1 | 3 (7) | | |
| Visit 2 (2 weeks) | Subject GAI n (%) | | | |
| | Worse | 0 | 0 | |
| | No Change | 0 | 0 | |
| | Improved | 17 (24) | 16 (23) | |
| | Much Improved | 26 (37) | 26 (37) | |
| | Very Much Improved | 28 (39) | 28 (40) | |
| | GAI at 9 months-4½ months n (%) | | | |
| | −1 | 6 (9) | | 1.000 |
| | 0 | 57 (81) | | |
| | 1 | 7 (10) | | |
| Visit 3 (4½ months) (before re-treatment) | Subject GAI n (%) | | | |
| | Worse | 0 | 0 | |
| | No Change | 0 | 1 (1) | |
| | Improved | 24 (35) | 21 (31) | |
| | Much Improved | 27 (40) | 29 (43) | |
| | Very Much Improved | 17 (25) | 17 (25) | |
| | GAI at 9 months-4½ months n (%) | | | |
| | −2 | 1 (1) | | 0.960 |
| | −1 | 5 (7) | | |
| | 0 | 55 (81) | | |
| | 1 | 6 (9) | | |
| | 2 | 1 (1) | | |
| Visit 4 (9 months) (before re-treatment) | Subject GAI n (%) | | | |
| | Worse | 1 (2) | 1 (2) | |
| | No Change | 0 | 3 (5) | |
| | Improved | 16 (25) | 16 (25) | |
| | Much Improved | 29 (45) | 30 (46) | |
| | Very Much Improved | 19 (29) | 15 (23) | |
| | GAI at 9 months-4½ months n (%) | | | |
| | −3 | 1 (2) | | 0.082 |
| | −1 | 14 (22) | | |
| | 0 | 44 (68) | | |
| | 1 | 5 (8) | | |
| | 2 | 1 (2) | | |
| Visit 5 (12 months) | Subject GAI n (%) | | | |
| | Worse | 0 | 0 | |
| | No Change | 1 (2) | 1 (2) | |
| | Improved | 11 (17) | 10 (16) | |
| | Much Improved | 30 (47) | 26 (41) | |
| | Very Much Improved | 22 (34) | 27 (42) | |
| | GAI at 9 months-4½ months n (%) | | | |
| | −1 | 7 (11) | | 0.263 |
| | 0 | 44 (69) | | |
| | 1 | 13 (20) | | |
| Visit 6 (15 months) | Evaluator GAI n (%) | | | |
| | Worse | 1 (2) | 1 (2) | |
| | No Change | 1 (2) | 0 | |
| | Improved | 10 (16) | 11 (17) | |
| | Much Improved | 33 (52) | 31 (48) | |
| | Very Much Improved | 19 (30) | 21 (33) | |
| | GAI at 9 months-4½ months n (%) | | | |
| | −1 | 5 (8) | | 0.581 |
| | 0 | 51 (80) | | |
| | 1 | 8 (13) | | |
| Visit 7 (18 months) (before re-treatment) | Evaluator GAI n (%) | | | |
| | Worse | 1 (2) | 1 (2) | |
| | No Change | 1 (2) | 2 (3) | |

TABLE 4.4-continued

Restylane Resorbption Rate Over Time
Subject's Global Aesthetic Improvement (GAI)
(Intent to Treat Population)

| Visit | GAI | Side Re-Treated 4½ months (N = 75) | Side Re-Treated 9 months (N = 75) | P-Value |
|---|---|---|---|---|
| | Improved | 10 (16) | 9 (14) | |
| | Much Improved | 23 (37) | 20 (32) | |
| | Very Much Improved | 28 (44) | 31 (49) | |
| | GAI at 9 months-4½ months n (%) | | | |
| | −1 | 6 (10) | | 0.807 |
| | 0 | 50 (79) | | |
| | 1 | 6 (10) | | |
| | 2 | 1 (2) | | |

A general summary of an analysis of all of the data for the entire population are depicted in FIGS. 3-7.

Study participants underwent a screening evaluation and initial treatment (FIG. 1, Visit 1). The two nasolabial folds were randomized for treatment so that one side is designated for re-treated with injectable filler at 4½ months the other at 9 months. At month 18 (FIG. 1, Visit 7) both nasolabial folds could be re-treated (if required).

At least two qualified personnel participated in the trial at each study center, for example: a Treating Investigator and an Evaluator. The Evaluator is blinded to treatment assignment and can only make the efficacy assessments in the study, which included also making the pre-treatment assessment of Wrinkle Severity, and deciding on when an optimal cosmetic result has been achieved. While not truly a double-blind study, the sides of the face assigned to the test and control treatments were masked from the Evaluator ("evaluator-blinded"). Due to the injection schedules, the treatment could not be masked from the study participant.

For each study participant, one nasolabial fold was randomly assigned to re-treatment at 4½ months with the test agent (injectable filler) and the opposite side was re-treated with the control treatment schedule at 9 months. The randomization was balanced within each treatment center, and was prepared by the study statistician.

A table outlining the schedule of procedures for the trial illustrated in this example is included in FIG. 2.

Screening evaluations were conducted prior to randomization and treatment (FIG. 1, Visit 1).

The objective of the initial treatment was to achieve an "optimal cosmetic result" on each side of the face. An "optimal result" is defined as the best possible cosmetic result that was obtained for an individual study participant with the two injectable implants (as determined by the Evaluating Investigator). After the initial implant session, the subject is evaluated after post treatment. Photography with standard Canfield system is done at all visits prior to treatments.

Following Visit 1 (Baseline/Screening), study participants returned for Visit 2 (week 2), Visit 3 (month 4½), Visit 4 (month 9), Visit 5 (month 12), Visit 6 (month 15), Visit 7 (month 18), Visit 8 (month 24), Visit 9 (month 27) and Visit 10 (month 30). If touch-ups were given at 2 weeks, a Follow-Up visit (Visit T), and another 2 Week Follow-Up visit (Visit 2) was scheduled 2 weeks after the touch-up treatment visit. Visit 3 is calculated from the last touch-up visit. At visit 3, one side of the nasolabial fold was re-treated to optimal cosmetic correction. At visit 4, the contralateral side was re-treated to optimal cosmetic correction. At visit 7, both nasolabial folds were re-treated to optimal cosmetic correction. At each follow-up visit, (T, 2, 3, 4, 5, 6, 7 8, 9 and 10), the subjects were assessed for the presence or absence of adverse events and the Evaluating Investigator and the Subject can make their evaluations based on the Severity Rating Scale and Global Aesthetic Improvement Scale. Photography with standard Canfield system was done at all visits prior to treatment.

The total duration of a subject's participation in the trial was approximately 29-30 months from the time of initial screening until the final follow-up.

Individuals eligible for inclusion in the study include the following: males or non-pregnant, non-breast feeding females aged 18 years or older, subjects seeking augmentation therapy for correction of bilateral nasolabial folds, subjects with a score of 3 or 4 on the Severity Rating Scale, subjects with the ability to understand and comply with the requirements of the trial, subjects willing to abstain from exclusionary procedures (e.g., further augmentation therapy, laser or chemical resurfacing; and BOTOX® injections below eye level; facelift) for the duration of the study.

The presence of any of the following could have excluded the potential study participant from entry into the trial: active or chronic skin disease, inflammation or related conditions, such as infection, psoriasis and herpes zoster near or on the nasolabial folds; subjects that have undergone procedures based on active dermal response (e.g. laser and chemical peeling procedures) within 6 months prior to study entry; use of any facial tissue augmenting therapy or aesthetic facial surgical therapy within nine (9) months prior to study entry, e.g. injection or other form of implantation of tissue augmenting substances, BOTOX® injections below the level of the eye-brows, and facelift; concomitant anticoagulant therapy, antiplatelet therapy, or a history of bleeding disorders; subjects who have previously experienced unanticipated adverse reactions when treated with hyaluronic acid based products; any condition which in the opinion of the investigator makes the subject unsuitable for inclusion (e.g., subjects not likely to avoid other treatments, subjects not likely to stay in the study for six months, or subjects anticipated to be unreliable; subjects with cancerous or pre-cancerous lesions in the area to be treated; and use of any investigational drugs or devices within 30 days prior to randomization.

The injectable filler used in this example was RESTYLANE® dermal filler. RESTYLANE® dermal filler is manufactured, packed and labelled by Q-Med AB, Uppsala, Sweden. RESTYLANE® dermal filler is a clear, colourless and transparent gel which includes 20 mg/ml of stabilized hyaluronic acid. The gel is sterile, viscoelastic and, free from products of animal origin. Pre-testing for hypersensitivity is not required. It is packaged in sterile 1.0 mL syringes and supplied with a sterilized 27G×½ inch needle. The product is dispersed in a physiological saline solution pH 7.

The treatment site was cleaned with a suitable antiseptic solution. RESTYLANE® dermal filler was administered using a thin gauge needle by injecting the material into the deep dermis and/or the surface layer of subcutis. If RESTYLANE® dermal filler was injected too deep or intramuscularly, the duration of the implant was shorter because of a higher hyaluronic acid turnover rate. Too superficial an injection can give blanching effects and bumps on the treatment site.

The injection technique with regard to the depth of injection and the administered quantity can vary. The linear threading technique was used to carefully lift up the wrinkle or fold, but some operators preferred a series of punctual injections or a combination of the two. During injection it was recommended that the eye of the needle face upwards. The contour of the needle should be visible but not the colour of it. One can inject RESTYLANE® dermal filler while pulling the needle slowly backwards. The injection stopped just before the needle was pulled out from the skin to prevent material from leaking out from the injection site. Defects were fully corrected, but not overcorrected. The injection site were massaged to conform to the contour of the surrounding tissues. For each treatment site a maximum dosage of about 1.5 ml per treatment session was recommended. If the treated area was swollen directly after the injection, melting ice was applied on the site for a short period. Dosage amounts used in the study are provided, inter alia, in Tables 4.5 and 4.6 below. In regard to Table 4.5, Completers were subjects with blinded evaluator scores available at all visits and with no missing data for injection volume. Treatment Schedule A involved the right side being re-treated with Restylane at 4½ months (left side untreated at 4½ months) and the left side being re-treated with Restylane at 9 months (right side untreated at 9 months). Treatment Schedule B involved the left side being re-treated with Restylane at 4½ months (right side untreated at 4½ months) and the right side being re-treated with Restylane at 9 months (left side untreated at 9 months). For Tables 4.5 and 4.6, the P-value was from a paired Student's t-test.

TABLE 4.5

Administration of Implant (ml) Over Time (Completers)

| Visit | | Re-Treated 4½ months (N = 60) | Re-Treated 9 months (N = 60) | Difference (9 – 4½ months) | P-value |
|---|---|---|---|---|---|
| Visit 1 | N | 60 | 60 | 60 | 0.609 |
| (Treatment) | Mean | 1.09 | 1.10 | 0.01 | |
| | Std Dev | 0.567 | 0.522 | 0.176 | |
| | Median | 1.00 | 1.00 | 0.00 | |
| | Min, Max | 0.1, 2.5 | 0.2, 2.5 | −0.5, 0.4 | |
| Visit T | N | 36 | 36 | 36 | 0.661 |
| (Touch-up) | Mean | 0.49 | 0.50 | 0.01 | |
| | Std Dev | 0.230 | 0.216 | 0.113 | |
| | Median | 0.50 | 0.50 | 0.00 | |
| | Min, Max | 0.2, 1.0 | 0.2, 1.0 | −0.2, 0.3 | |
| Visit 3 | N | 60 | 0 | 0 | |
| (4½ months) | Mean | 0.71 | | | |
| (before | Std Dev | 0.305 | | | |
| re-treatment) | Median | 0.80 | | | |
| | Min, Max | 0.2, 1.4 | | | |
| Visit 3 | N | 0 | 60 | 0 | |
| (4½ months) | Mean | | 0.67 | | |
| (before | Std Dev | | 0.359 | | |
| re-treatment) | Median | | 0.60 | | |
| | Min, Max | | 0.1, 2.0 | | |
| Total | N | 60 | 60 | 60 | 0.657 |
| Volume | Mean | 2.09 | 2.07 | −0.02 | |
| Injected | Std Dev | 0.863 | 0.836 | 0.376 | |
| | Median | 2.00 | 2.10 | 0.00 | |
| | Min, Max | 0.7, 4.0 | 0.9, 4.7 | −0.8, 1.2 | |

TABLE 4.6

Administration of Implant (ml) Over Time (Intent to Treat Population)

| Visit | | Re-Treated 4½ months (N = 75) | Re-Treated 9 months (N = 75) | Difference (9 – 4½ months) | P-value |
|---|---|---|---|---|---|
| Visit 1 | N | 75 | 75 | 75 | 0.353 |
| (Treatment) | Mean | 1.08 | 1.09 | 0.02 | |
| | Std Dev | 0.603 | 0.559 | 0.161 | |
| | Median | 1.00 | 1.00 | 0.00 | |
| | Min, Max | 0.1, 2.5 | 0.2, 2.5 | −0.5, 0.4 | |
| Visit T | N | 44 | 44 | 44 | 0.660 |
| (Touch-up) | Mean | 0.47 | 0.48 | 0.01 | |
| | Std Dev | 0.220 | 0.208 | 0.102 | |
| | Median | 0.50 | 0.50 | 0.00 | |
| | Min, Max | 0.2, 1.0 | 0.2, 1.0 | −0.2, 0.3 | |
| Visit 3 | N | 67 | 0 | 0 | |
| (4½ months) | Mean | 0.71 | | | |
| (before | Std Dev | 0.330 | | | |
| re-treatment) | Median | 0.80 | | | |
| | Min, Max | 0.2, 1.8 | | | |
| Visit 4 | N | 0 | 63 | 0 | |
| (9 months) | Mean | | 0.67 | | |
| (before | Std Dev | | 0.356 | | |
| re-treatment) | Median | | 0.60 | | |
| | Min, Max | | 0.1, 2.0 | | |
| Total | N | 75 | 75 | 75 | 0.206 |
| Volume | Mean | 1.99 | 1.93 | −0.06 | |
| Injected | Std Dev | 0.902 | 0.863 | 0.389 | |
| | Median | 2.00 | 2.00 | 0.00 | |
| | Min, Max | 0.2, 4.0 | 0.4, 4.7 | −1.0, 1.2 | |

In this study in this example, a maximum of 100% correction was administered. It was noted as important not to overcorrect.

The trial in this example included two administrations of the implants by the Treating Investigator. As a result, compliance did not require further assessment.

Before the treatment, the subject's need for pain relief can optionally be assessed. Local or topical anaesthetics or a dental block can be used, if needed. Any such use should be recorded in the CRF.

Except as noted below, concomitant medications or other treatments can be utilized when medically necessary. Any concomitant medication, including over-the-counter (OTC) medications administered, or any concomitant procedures such as surgery/biopsy or diagnostic evaluations performed during the study were recorded on the case report form (CRF). The generic name of the concomitant medication (or a description of the procedure) and the reason for its use can also be provided on the CRF. Administration of anticoagulants (e.g., warfarin) or inhibitors of platelet aggregation (e.g., aspirin or other nonsteroidal anti-inflammatory drugs) are excluded beginning three weeks prior to the treatment visit and extending until the injection sites are completely healed (unless medically necessary, this exclusion should extend for at least four weeks after treatment).

At least one independent Evaluating Investigator is designated at each study site. This investigator is blinded to treatment assignment and can perform all of the efficacy evaluations. The Evaluating Investigator can make the efficacy assessments in the study, and may take part in the care of the subject after the injection.

A Severity Rating Scale was used to assess the visual appearance of the nasolabial folds. It is an assessment of wrinkle severity at a certain time-point and is not based on a comparison to the pre-treatment appearance. The assessments were made by the blinded, independent Evaluating Investigator and used as the primary efficacy measurement in the study. The Evaluating Investigator rated each nasolabial fold separately (right and left) for severity using the following categorical scale (Table 4.7).

TABLE 4.7

Severity Rating Scale

| Score | Description |
|---|---|
| 5 | Extreme: Extremely deep and long folds; detrimental to facial appearance. 2-4 mm visible v-shaped fold when stretched. Unlikely to have satisfactory correction with injectable implant alone. |
| 4 | Severe: Very long and deep folds; prominent facial feature. Less than 2 mm visible fold when stretched. Significant improvement is expected from injectable implant |
| 3 | Moderate: Moderately deep folds; clear facial feature visible at normal appearance but not when stretched. Excellent correction is expected from injectable implant. |
| 2 | Mild: Shallow but visible fold with a slight indentation; minor facial feature. Implant is expected to produce a slight improvement in appearance. |
| 1 | Absent: no visible fold; continuous skin line |

Each score in the Severity Rating Scale was exemplified by a set of three photographs of nasolabial folds. A favorable change of at least one score in the Severity Rating Scale is defined as a clinical significant improvement.

The assessment was performed at the treatment visit (Visit 1), two weeks after treatment (Visit 2) and at each subsequent Follow-Up Visit. During visits where treatment is administered, the severity is rated prior to injection.

The Severity Rating Scale was also used by the Treating Investigator at study entry to assess the inclusion criteria.

The subjects can assess the visual appearance of each nasolabial fold separately (right and left) using the following categorical severity scale (Table 4.8).

TABLE 4.8

Severity Rating Scale

| Score | Description |
|---|---|
| 5 | Extreme: Extremely deep and long folds; detrimental to facial appearance. 2-4 mm visible v-shaped fold when stretched. |
| 4 | Severe: Very long and deep folds; prominent facial feature. Less than2 mm visible fold when stretched. |
| 3 | Moderate: Moderately deep folds; clear facial feature visible at normal appearance but not when stretched. |
| 2 | Mild: Shallow but visible fold with a slight indentation; minor facial feature. |
| 1 | Absent: no visible fold; continuous skin line |

The assessment can represent wrinkle severity at a certain time-point and not be based on a comparison to the pre-treatment defect level. Each score in the Severity Rating Scale is exemplified by a set of three photographs of nasolabial folds. A favourable change of at least one score in the Severity Rating Scale is defined as a clinically significant improvement.

The assessments were performed at the treatment visit (Visit 1), after optimal cosmetic results had been obtained (Visit 2) and at each subsequent visit. During visits where treatment was administered, the severity was rated prior to injection.

The Evaluating Investigator rated each nasolabial fold for global aesthetic improvement, i.e. improvement from pre-treatment appearance, using the following categorical scale (Table 4.9).

TABLE 4.9

| Rating | Definition |
|---|---|
| Very Much Improved | Optimal cosmetic result for the implant in this subject. |
| Much Improved | Marked improvement in appearance from the initial condition, but not completely optimal for this subject. |
| Improved | Obvious improvement in appearance from the initial condition. |
| No Change | The appearance is essentially the same as baseline. |
| Worse | The appearance is worse than the original condition. |

The Evaluating Investigator made this assessment in view of the overall cosmetic result for each contra lateral fold. The ratings were correlated with the actions that would generally be considered in the normal course of practice. The Evaluating Investigator could optionally review the pre-treatment archival photograph (obtained prior to injection of the implants at Visit 1) at each visit to aid in the assessment.

The assessment was performed two weeks after treatments (Visit 2) and at each subsequent visit.

The subjects also rated the global aesthetic improvement of each nasolabial fold, relative to pre-treatment appearance, using the above categorical scale.

The subject was asked to evaluate the overall improvement in the appearance of each nasolabial fold. The subject was instructed to select the one rating which best describes the degree to which the appearance of nasolabial fold has been improved by the implant relative to pre-treatment. The subject could have reviewed the pre-treatment archival photograph (obtained prior to injection of the implants at Visit 1) at each visit to aid in the assessment.

The assessment is performed after optimal cosmetic result has been obtained (Visit 2) and at each subsequent visit.

Photographs taken at the "Screening and Treatment Visit" (Visit 1) served as reference for the Evaluator's and Subject's post-treatment assessment of Global Aesthetic Improvement. The photographs were obtained in an as standardized manner as possible, in accordance with the practice of the study facility. The set of photographs could have included at least one direct frontal view centered on the study participant's face (both nasolabial folds should be clearly visible). Each photograph should have been labeled with the study participant's randomization number, initials and date of photograph. Archival photographs are taken at scheduled visits during the study (to document treatment result).

Statistical analyses were performed using the SAS® system. Summary tables and data listings were prepared using SAS®. Subjects were randomized to RESTYLANE® dermal filler on one side of the face with re-treatment at 4½ months and re-treatment at 9 months on the other side. One side of the face is labeled the right side and the other side is labeled the left side.

Visits occurred at pre-treatment, initial treatment (Visit 1), two weeks (Visit 2) and at four and one-half months (visit 3), nine months (visit 4) and twelve months (visit 5), fifteen months (Visit 6), eighteen months (Visit 7), twenty-four months (Visit 8), twenty-seven months (Visit 9) and thirty months (Visit 10). Effort was made to have all visits occur on time. For the subsequent visits, a window of +/− one week can be allowed.

The Severity Rating Scale and the Global Aesthetic Improvement Scale are ordered categorical measures. The primary efficacy evaluation was based on a responder criterion. A subject was defined as a responder for the treatment (wrinkle) if there was an improvement of at least one step in the Severity Rating Scale (assessed by the investigator) from the value prior to treatment (visit 1) to the value at 4½, 9 and 12 month respectively (visit 3, 4, and 5).

Three analysis populations were defined for this trial: The safety population included all subjects who received an implant with either the test or control device. The Intent-to-treat (ITT) population included all subjects, who were randomized and treated. The Per-protocol (PP) population included all subjects in the intent-to-treat population who had all efficacy evaluations at all time points and who had no major protocol deviations.

Summary of the Results for the Above Example

NASHA's effective correction of nasolabial folds persisted for at least 18 months post-initial treatment and at least 9 to 13.5 months post-retreatment, regardless of re-treatment schedule. Almost all patients (97%) had at least 1 grade improvement at 18 months (13.5 or 9 months post-re-treatment) and many had 2 grades improvement. Early re-treatment can be superior as patients do not experience an increase in wrinkle severity before receiving a second treatment and the response is maintained for at least 1 year. The earlier re-treatment appears to maintain tissue expansile tension and slow gel resorption so that results are the same regardless of re-treatment schedule. The long lasting effect reported here can be amplified by injection-stimulated collagen production and collagen breakdown inhibition that outlasts the filling of space by the injected gel.

Figure 5:
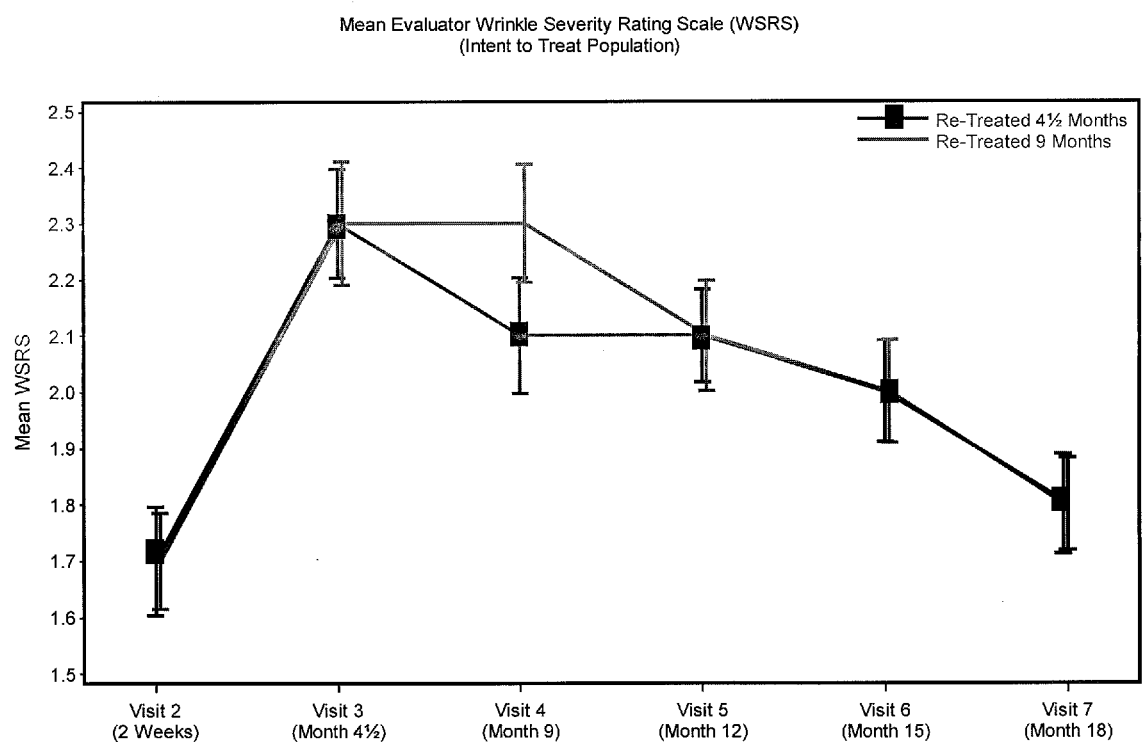
FIG. 5 is a line graph summarizing results from a trial study. The line graph shows a comparison of wrinkle severity from re-treatment at 4.5 months with re-treatment after 9 months at the indicated time points.
Figure 6:
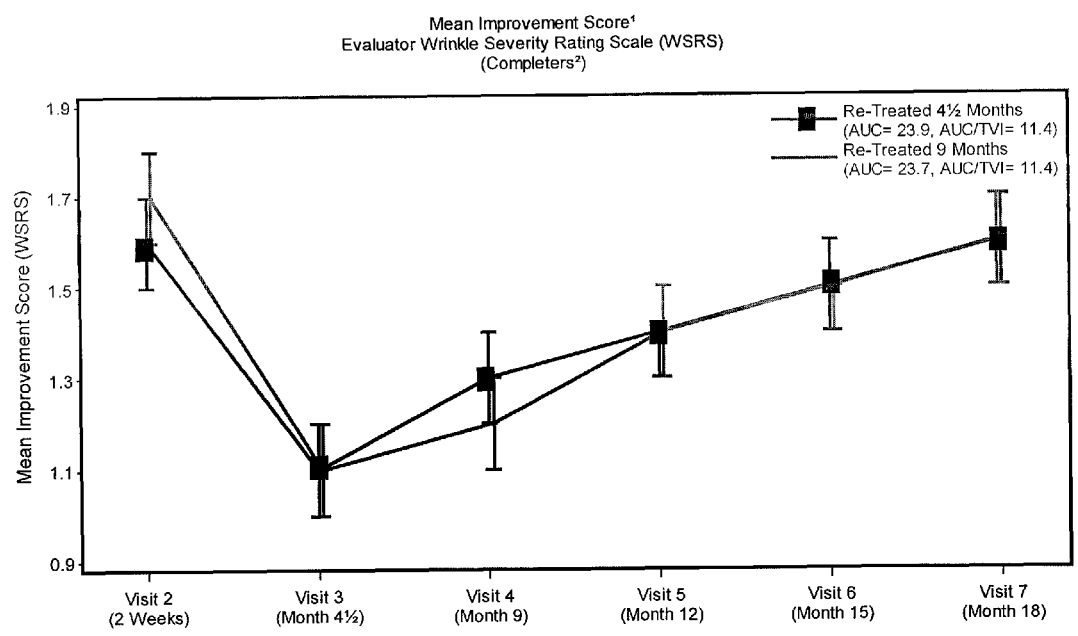
FIG. 6 is a line graph summarizing results from a trial study. The line graph shows a comparison of the improvement resulting from re-treatment at 4.5 months with re-treatment after 9 months at the indicated time points. The data used to prepare the curves represents the completers subset of the data.
Figure 7:
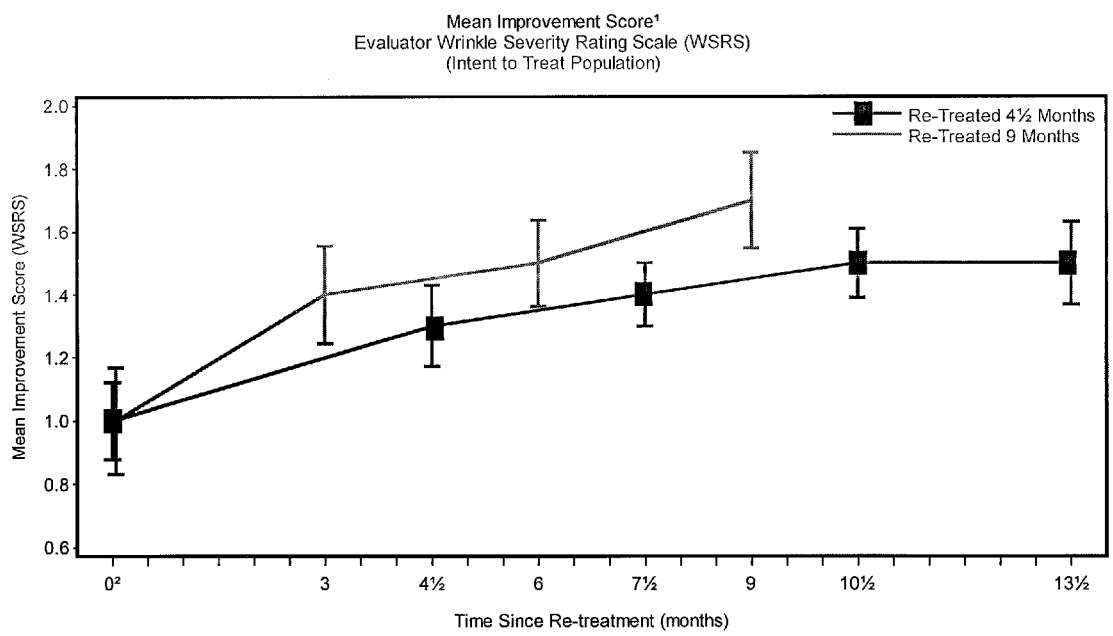
FIG. 7 is a line graph summarizing results from a trial study. The line graph shows a comparison of the improvement resulting from re-treatment at 4.5 months with re-treatment after 9 months at the indicated time points. The zero time in the graph represents the time immediately following the re-treatment time.

An additional summary of these results is presented in FIGS. 3-7. FIG. 3 summarizes the results for Responder analysis of the wrinkle severity rating score between the 4½ and 9 month re-treatment schedule over time. FIG. 4 summarizes the mean improvement score results for the wrinkle severity rating score between the 4½ and 9 month re-treatment schedule over time. FIG. 5 summarizes the results for the wrinkle severity rating score between the 4½ and 9 month re-treatment schedule over time. FIG. 6 summarizes the mean improvement score results for the completers for the wrinkle severity rating score between the 4½ and 9 month re-treatment schedule over time. FIG. 7 summarizes the mean improvement score results for the wrinkle severity rating score between the 4½ and 9 month re-treatment schedule over time. The "0" time period is the time period starting after the re-treatment step.

In some embodiments, some of the above embodiments can be employed to provide Evaluator and participant mean Wrinkle Severity Rating Scale score improvement of 0.7 grades at 2 weeks and of 1.6 grades at 18 months and of 0.7 to 1.0 grades across 7 visits, respectively. In some embodiments, Evaluator and participant Global Aesthetic Improvement Scale ratings can provide improvement from 2.4 points at 2 weeks to 3.7 points at 18 months and from 2.4 to 3.2 points across the 7 visits, respectively. In some embodiments, any improvements or results demonstrated in FIGS. 3-7 can be achieved through the use of various embodiments disclosed herein.

Example 5

Moderate to Extreme Baseline Population of Example 4

The data presented in the Examples above included the results from all subjects included in the population where data were available for the relevant endpoints and follow-up visits under evaluation. However, such an analysis can overly simplify the actual results, missing the true effectiveness of the method on subjects that can receive larger benefits from the method. Thus, to more accurately review the results in the subjects with more extensive wrinkles (e.g., a higher WSRS starting score), a subset of the data, which only included subjects who had moderate to severe WSRS scores at baseline, was examined. This example, therefore, excluded one subject with mild WSRS at baseline in the analysis of the Blinded Evaluator's assessment of WSRS and five subjects in the analysis of the subject's assessment of WSRS at the 4½ V month re-treatment side. One subject with a mild WSRS score at baseline was excluded from the analysis of the subject's assessment of WSRS at the 9 month re-treatment side.

The proportion of subjects with at least one grade improvement in WSRS scores as assessed by the Blinded Evaluator and subject at each visit is summarized in Table 5.1 for the Blinded Evaluator and in Table 5.2 for the subject. At 18 months, the mean improvement from baseline in WSRS score was ≧1 grade for both re-treated sides by Blinded Evaluator and subject assessments. Subject assessment of their nasolabial folds at 18 months showed at least one grade improvement on the WSRS in 85% of subjects on the 4½ month re-treated side and 78% on the 9 month re-treated side. The mean change from baseline was statistically significant ($p<0.001$) in both re-treated sides for both Blinded Evaluator and subject assessments.

TABLE 5.1

Blinded Evaluator's Assessment - Proportion of Subjects with at Least One Grade Improvement in WSRS from Baseline

| | Side Assigned to Re-treatment at 4½ Months | | | Side Assigned to Re-treatment at 9 Months | | |
|---|---|---|---|---|---|---|
| Visit | n/N | p ± s.e.* % | 95% CI† | n/N | p ± s.e. % | 95% CI |
| 2 Weeks | 66/71 | 93.0 ± 3.0 | 84.3-97.7% | 69/71 | 97.2 ± 2.0 | 90.2-99.7% |
| 4½ Months | 56/66 | 84.9 ± 4.4 | 73.9-92.5% | 54/67 | 80.6 ± 4.8 | 69.1-89.2% |
| 9 Months | 56/64 | 87.5 ± 4.1 | 76.9-94.5% | 53/65 | 81.5 ± 4.8 | 70.0-90.1% |
| 12 Months | 60/62 | 96.8 ± 2.2 | 88.8-99.6% | 57/63 | 90.5 ± 3.7 | 80.4-96.4% |

TABLE 5.1-continued

Blinded Evaluator's Assessment - Proportion of Subjects with
at Least One Grade Improvement in WSRS from Baseline

| | Side Assigned to Re-treatment at 4½ Months | | | Side Assigned to Re-treatment at 9 Months | | |
|---|---|---|---|---|---|---|
| Visit | n/N | p ± s.e.* % | 95% CI[†] | n/N | p ± s.e. % | 95% CI |
| 15 Months | 58/63 | 92.1 ± 3.4 | 82.4-97.4% | 58/64 | 90.6 ± 3.6 | 80.7-96.5% |
| 18 Months | 61/63 | 96.8 ± 2.2 | 89.0-99.6% | 61/64 | 95.3 ± 2.6 | 86.9-99.0% |

*Standard error;
[†]Exact 95% confidence interval (CI).
Note:
At visits where subjects were re-treated, grading was performed prior to re-treatment.

As assessed by the Blinded Evaluator, a large majority of subjects had at least one grade improvement in WSRS score at every follow-up visit, ranging from about 88% to 97% for every visit after re-treatment (i.e., WSRS scores at 9, 12, 15, and 18 month visits for the 4½ months re-treatment side and WSRS scores at 12, 15, and 18 month visits for the 9 months re-treatment side). The lower limits of the confidence intervals at every time point after re-treatment was >76%. At 18 months (more than one year after re-treatment at 4½ months and 9 months after re-treatment of the other side at 9 months), the proportion of subjects with at least one grade improvement in WSRS was similar between the two sides (97% of the 4½ month re-treated side and 95% of the 9-month re-treated side).

A large majority of subjects also assessed the WSRS scores as at least one grade improvement; e.g., for NLFs re-treated at 4½ months, about 80-85% of subjects rated those NLFs as having at least one grade improvement at every visit after re-treatment. The lower limits of the confidence intervals at every time point after re-treatment was >62%. At 18 months, the proportion of subjects with at least one grade improvement in WSRS was similar between the two sides (85% of the 4½ month re-treated side and 78% of the 9-month re-treated side).

TABLE 5.2

Subject's Assessment - Proportion of Subjects with at Least
One Grade Improvement in WSRS from Baseline

| | Side Assigned to Re-treatment at 4½ Months | | | Side Assigned to Re-treatment at 9 Months | | |
|---|---|---|---|---|---|---|
| Visit | n/N | p ± s.e.* % | 95% CI[†] | n/N | p ± s.e. % | 95% CI |
| 2 Weeks | 58/68 | 85.3 ± 4.3 | 74.6-92.7% | 60/70 | 85.7 ± 4.2 | 75.3-92.9% |
| 4½ Months | 42/62 | 67.7 ± 5.9 | 54.7-79.1% | 41/66 | 62.1 ± 6.0 | 49.3-73.8% |
| 9 Months | 48/60 | 80.0 ± 5.2 | 67.7-89.2% | 44/64 | 68.8 ± 5.8 | 55.9-79.8% |
| 12 Months | 49/59 | 83.1 ± 4.9 | 71.0-91.6% | 56/63 | 88.9 ± 4.0 | 78.4-95.4% |
| 15 Months | 47/59 | 79.7 ± 5.2 | 67.2-89.0% | 47/63 | 74.6 ± 5.5 | 62.1-84.7% |
| 18 Months | 50/59 | 84.8 ± 4.7 | 73.0-92.8% | 49/63 | 77.8 ± 5.2 | 65.5-87.3% |

*Standard error;
[†]Exact 95% confidence interval (CI).
Note:
At visits where subjects were re-treated, grading was performed prior to re-treatment.

The proportion of subjects with at least one grade improvement in WSRS scores as assessed by the Blinded Evaluator, the IPR, and subject at each visit is demonstrated graphically in FIG. 8 for the side of the face re-treated at 4½ months and FIG. 9 for the side of the face re-treated at 9 months.
Mean WSRS and Mean Improvement in WSRS from Baseline by Visit The mean WSRS scores and mean improvement from baseline as assessed by the Blinded Evaluator and subject at each visit are summarized in Table 5.3 for the Blinded Evaluator and in Table 5.4 for the subject.

For the Blinded Evaluator assessment, the mean improvement from baseline in WSRS score was more than 1 grade for each side at all time points. At 18 months (13.5 months after the 4½ month re-treatment, and 9 months after the 9 month re-treatment), the mean change from baseline in WSRS for both re-treated sides was similar to the change from baseline noted at 2 weeks after re-treatment (1.6 to 1.7 at 18 months; 1.7 at 2 weeks after re-treatment).

For the subject assessment, the mean improvement from baseline in WSRS score ranged from about 0.9 to 1.3 for the 4½ month re-treated side and about 0.8 to 1.3 for the 9 month re-treated side. At 18 months, the mean change from baseline in WSRS for both re-treated sides was similar to the change from baseline noted at 2 weeks after re-treatment (1.1 at 18 months; 1.2 to 1.3 at 2 weeks after re-treatment).

The mean change from baseline at all visits was statistically significant (p<0.001) for all follow-up Blinded Evaluator and subject assessments.

TABLE 5.3

Blinded Evaluator's Assessment - Mean WSRS and Mean Improvement in WSRS from Baseline

| | Side Assigned to Re-treatment at 4½ Months | | Side Assigned to Re-treatment at 9 Months | |
| --- | --- | --- | --- | --- |
| Visit | N | WSRS Mean ± SD | Change from Baseline Mean ± SD* | N | WSRS Mean ± SD | Change from Baseline Mean ± SD* |
| Screening | 74 | 3.4 ± 0.60 | — | 75 | 3.4 ± 0.60 | — |
| 2 Weeks | 71 | 1.7 ± 0.81 | 1.7 ± 0.81 | 71 | 1.7 ± 0.72 | 1.7 ± 0.71 |
| 4½ Months | 66 | 2.3 ± 0.78 | 1.1 ± 0.72 | 67 | 2.3 ± 0.89 | 1.1 ± 0.83 |
| 9 Months | 64 | 2.2 ± 0.82 | 1.3 ± 0.73 | 65 | 2.3 ± 0.85 | 1.1 ± 0.84 |
| 12 Months | 62 | 2.1 ± 0.65 | 1.3 ± 0.65 | 63 | 2.1 ± 0.78 | 1.3 ± 0.80 |
| 15 Months | 63 | 2.0 ± 0.72 | 1.5 ± 0.74 | 64 | 2.0 ± 0.73 | 1.4 ± 0.75 |
| 18 Months | 63 | 1.8 ± 0.65 | 1.7 ± 0.74 | 64 | 1.8 ± 0.70 | 1.6 ± 0.77 |

*Mean changes from baseline are significantly different from 0 at all follow-up visits (paired t-test p < 0.001).

In regard to the present WSRS tables, WSRS of 1=Absent; 2=Mild; 3=Moderate; 4=Severe; and 5=Extreme. At visits where subjects were re-treated, grading was performed prior to re-treatment.

TABLE 5.4

Subject's Assessment - Mean WSRS and Mean Improvement in WSRS from Baseline

| | Side Assigned to Re-treatment at 4½ Months | | Side Assigned to Re-treatment at 9 Months | |
| --- | --- | --- | --- | --- |
| Visit | N | WSRS Mean ± SD | Change from Baseline Mean ± SD* | N | WSRS Mean ± SD | Change from Baseline Mean ± SD* |
| Screening | 70 | 3.4 ± 0.54 | — | 74 | 3.4 ± 0.58 | — |
| 2 Weeks | 68 | 2.1 ± 0.69 | 1.3 ± 0.78 | 70 | 2.1 ± 0.75 | 1.2 ± 0.75 |
| 4½ Months | 62 | 2.5 ± 0.74 | 0.9 ± 0.79 | 66 | 2.5 ± 0.79 | 0.8 ± 0.87 |
| 9 Months | 60 | 2.2 ± 0.73 | 1.2 ± 0.76 | 64 | 2.5 ± 0.66 | 0.9 ± 0.75 |
| 12 Months | 59 | 2.2 ± 0.71 | 1.2 ± 0.77 | 63 | 2.1 ± 0.70 | 1.3 ± 0.76 |
| 15 Months | 59 | 2.4 ± 0.61 | 1.0 ± 0.72 | 63 | 2.4 ± 0.73 | 0.9 ± 0.83 |
| 18 Months | 59 | 2.3 ± 0.70 | 1.1 ± 0.67 | 63 | 2.3 ± 0.68 | 1.1 ± 0.76 |

*Mean changes from baseline are significantly different from 0 at all follow-up visits (paired t-test p < 0.001).

The mean improvement from baseline as assessed by the Blinded Evaluator, IPR, and subject at each visit is graphically presented in FIG. 10 for the side of the face re-treated at 4½ months and FIG. 11 for the side of the face re-treated at 9 months.

Improvement from Baseline was also assessed using the Global Aesthetic Improvement Scale (GAIS) for Treating Investigator and subject. The GAIS can be converted into numerical values as follows: 0—Worse; 1—No Change; 2—Improved; 3—Much Improved; 4—Very Much Improved. At 18 months for the Treating Investigator assessment, the mean GAIS was the same (3.7) for both re-treated sides. Similarly, at 18 months for the subject assessment, the mean GAIS was the same (3.2) for both re-treated sides. These scores both indicate "Much Improved" on the mean GAIS score, confirming the improvement in wrinkle severity evaluated by the WSRS. Tables 5.5 and 5.6 below provide the proportion of subjects with at least on grade improvement in Global Aesthetic Improvement Scale (GAIS) from baseline by visit. Table 5.5 shows the treating investigator's assessment, and Table 5.6 shows the subject's assessment.

Improvement from baseline was consistently affirmed by both Treating Investigator and subject. Most subjects assessed by the Treating Investigator (98% to 100%) and subjects (94% to 100%) had at least a one grade improvement from baseline on the GAIS at all follow-up visits. The mean GAIS scores as assessed by the Treating Investigators and subjects ranged from 3.0 to 3.7 (Much Improved) for both treated sides at all visits after re-treatment.

TABLE 5.5

Treating Investigator's assessment

| Visit | N | Side Assigned to Re-treatment at 4½ Months | Side Assigned to Re-treatment at 9 Months |
| --- | --- | --- | --- |
| 2 Weeks | 72 | 72 (100%) | 71 (100%)* |
| 4½ Months | 67 | 67 (100%) | 66 (98.5%) |
| 9 Months | 65 | 64 (98.5%) | 64 (98.5%) |
| 12 Months | 64 | 64 (100%) | 64 (100%) |
| 15 Months | 64 | 64 (100%) | 64 (100%) |
| 18 Months | 63 | 63 (100%) | 62 (98.4%) |

*Based on data from 71 subjects.

TABLE 5.6

Subject's Assessment

| Visit | N | Side Assigned to Re-treatment at 4½ Months | Side Assigned to Re-treatment at 9 Months |
| --- | --- | --- | --- |
| 2 Weeks | 71 | 71 (100%) | 70 (100%)* |
| 4½ Months | 67 | 67 (100%) | 66 (98.5%) |
| 9 Months | 65 | 64 (98.5%) | 61 (93.9%) |
| 12 Months | 64 | 63 (98.4%) | 63 (98.4%) |
| 15 Months | 64 | 62 (96.9%) | 63 (98.4%) |
| 18 Months | 64 | 62 (96.9%) | 61 (95.3%) |

*Based on data from 70 subjects

Tables 5.7 and 5.8 below provide the mean GAIS by visit. Table 5.7 shows the treating investigator's assessment, and Table 5.8 shows the subject's assessment.

TABLE 5.7

Treating Investigator's Assessment

| Visit | N | Side Assigned to Re-treatment at 4½ Months Mean ± SD* | Side Assigned to Re-treatment at 9 Months Mean ± SD* |
| --- | --- | --- | --- |
| 2 Weeks | 72 | 3.6 ± 0.55 | 3.6 ± 0.55** |
| 4½ Months | 67 | 3.4 ± 0.65 | 3.4 ± 0.71 |
| 9 Months | 65 | 3.5 ± 0.69 | 3.4 ± 0.71 |
| 12 Months | 64 | 3.5 ± 0.62 | 3.5 ± 0.62 |

TABLE 5.7-continued

Treating Investigator's Assessment

| Visit | N | Side Assigned to Re-treatment at 4½ Months Mean ± SD* | Side Assigned to Re-treatment at 9 Months Mean ± SD* |
|---|---|---|---|
| 15 Months | 64 | 3.7 ± 0.49 | 3.6 ± 0.52 |
| 18 Months | 63 | 3.7 ± 0.54 | 3.7 ± 0.57 |

*Mean improvements are significantly different from 1 ("no change") at all follow-up visits (paired t-test p < 0.001).
**Based on data from 71 subjects.

TABLE 5.8

Subject's Assessment

| Visit | N | Side Assigned to Re-treatment at 4½ Months Mean ± SD* | Side Assigned to Re-treatment at 9 Months Mean ± SD* |
|---|---|---|---|
| 2 Weeks | 71 | 3.2 ± 0.79 | 3.2 ± 0.78** |
| 4½ Months | 67 | 2.9 ± 0.77 | 2.9 ± 0.79 |
| 9 Months | 65 | 3.0 ± 0.83 | 2.8 ± 0.89 |
| 12 Months | 64 | 3.1 ± 0.75 | 3.2 ± 0.77 |
| 15 Months | 64 | 3.1 ± 0.81 | 3.1 ± 0.80 |
| 18 Months | 64 | 3.2 ± 0.88 | 3.2 ± 0.92 |

*Mean improvements are significantly different from 1 ("no change") at all follow-up visits (paired t-test p < 0.001).
**Based on data from 70 subjects.

TABLE 5.10

Independent Reviewers' Assessment

| | Side Assigned to Re-treatment at 4½ Months | | | Side Assigned to Re-treatment at 9 Months | | |
|---|---|---|---|---|---|---|
| Visit | n/N | p ± s.e.* % | 95% CI† | n/N | p ± s.e. % | 95% CI |
| 2 Weeks | 44/60 | 73.3 ± 5.7 | 60.3-83.9% | 49/60 | 81.7 ± 5.0 | 69.6-90.5% |
| 4½ Months | 38/54 | 70.4 ± 6.2 | 56.2-82.0% | 38/53 | 71.7 ± 6.2 | 57.7-83.2% |
| 9 Months | 42/53 | 79.3 ± 5.6 | 65.9-89.2% | 35/53 | 66.0 ± 6.5 | 51.7-78.5% |
| 12 Months | 40/51 | 78.4 ± 5.8 | 64.7-88.7% | 42/50 | 84.0 ± 5.2 | 70.9-92.8% |
| 15 Months | 46/53 | 86.8 ± 4.7 | 74.4-94.5% | 44/52 | 84.6 ± 5.0 | 71.9-93.1% |
| 18 Months | 40/53 | 75.5 ± 5.9 | 63.9-87.1% | 42/51 | 82.4 ± 5.3 | 69.1-91.6% |

*Standard error.
†Exact 95% confidence interval (CI).

A panel of three Independent Photographic Reviewers (IPR) evaluated WSRS scores of photographs taken at all study visits. Each reviewer reviewed the photographs independently and assigned a WSRS to each photograph. This analysis resulted in about 76% to 87% of subjects achieving at least a one grade improvement from baseline in WSRS scores and a mean change from baseline in WSRS score that was greater than one grade improvement at 18 months. Table 5.9 below provides the results from the independent photographic review.

For analysis of mean WSRS, the median WSRS of each of the 3 independent reviews was calculated and used in the analysis. For analysis of the mean change in WSRS, the change in WSRS from baseline was first calculated for each subject within each reviewer, then the median of the change scores was calculated and used in the analysis. NLFs with mild WSRS at baseline were excluded from the analysis.

The proportion of subjects achieving at least a one grade improvement from baseline after re-treatment as assessed by IPR was from 76% to 87% for the 4½ month re-treated side and 82% to 85% for the 9 month side. At 18 months, the mean change from baseline in WSRS for both re-treated sides was ≧1 grade improvement from baseline, similar to the change from baseline noted at 2 weeks after re-treatment.

TABLE 5.9

Baseline Assessment

| Wrinkle Severity Rating Scale (IPR) | Side assigned to re-treatment at 4½ months | Side assigned to re-treatment at 9 months |
|---|---|---|
| Number of Subjects | 73 | 73 |
| 1 - Absent | 0 | 0 |
| 2 - Mild | 12 (16.4%) | 12 (16.4%) |
| 3 - Moderate | 40 (54.8%) | 39 (53.4%) |
| 4 - Severe | 16 (21.9%) | 16 (21.9%) |
| 5 - Extreme | 5 (6.8%) | 6 (8.2%) |
| Mean ± SD | 3.2 ± 0.79 | 3.2 ± 0.82 |
| Median | 3 | 3 |

Table 5.10 below depicts the proportion of subjects with at least one grade improvement in WSRS from baseline by visit (independent reviewers' assessment).

Table 6.11 below depicts the mean WSRS and mean improvement in WSRS from baseline by visit (independent reviewers' assessment).

TABLE 5.11

Independent Reviewers' Assessment

| | Side Assigned to Re-treatment at 4½ Months | | | Side Assigned to Re-treatment at 9 Months | | |
|---|---|---|---|---|---|---|
| Visit | N | WSRS Mean ± SD | Change from Baseline Mean ± SD* | N | WSRS Mean ± SD | Change from Baseline Mean ± SD* |
| Screening | 61 | 3.4 ± 0.64 | — | 61 | 3.5 ± 0.67 | — |
| 2 Weeks | 60 | 2.6 ± 0.82 | 1.0 ± 0.74 | 60 | 2.5 ± 0.82 | 1.0 ± 0.71 |
| 4½ Months | 54 | 2.7 ± 0.75 | 0.9 ± 0.63 | 53 | 2.7 ± 0.85 | 0.9 ± 0.75 |
| 9 Months | 53 | 2.4 ± 0.80 | 1.0 ± 0.69 | 53 | 2.7 ± 0.74 | 0.8 ± 0.67 |
| 12 Months | 51 | 2.5 ± 0.80 | 0.9 ± 0.64 | 50 | 2.5 ± 0.87 | 1.2 ± 0.75 |

TABLE 5.11-continued

Independent Reviewers' Assessment

| | Side Assigned to Re-treatment at 4½ Months | | | Side Assigned to Re-treatment at 9 Months | | |
|---|---|---|---|---|---|---|
| Visit | N | WSRS Mean ± SD | Change from Baseline Mean ± SD* | N | WSRS Mean ± SD | Change from Baseline Mean ± SD* |
| 15 Months | 53 | 2.4 ± 0.86 | 1.1 ± 0.67 | 52 | 2.6 ± 0.93 | 1.1 ± 0.87 |
| 18 Months | 53 | 2.5 ± 0.82 | 1.1 ± 0.68 | 51 | 2.5 ± 0.77 | 1.1 ± 0.70 |

*Mean changes from baseline are significantly different from 0 at all follow-up visits (paired t-test p < 0.001).

In summary, at 18 months, the proportion of subjects maintaining at least one grade improvement was 97% (Blinded Evaluator) for the 4½ month re-treated side, which was similar to the response rate of the 9-month re-treatment side at 18 months (95%). Although subject scoring was slightly lower than by Blinded Evaluator assessment, the large majority of subjects self-assessed their WSRS at least one grade improvement. The trend for subjects to evaluate themselves more pessimistically than medical professionals is commonly observed in other studies. Nonetheless, at 18 months, about 85% of subjects indicated at least one grade improvement on the WSRS on the 4½ month re-treated side and about 78% on the 9 month re-treated side.

For the Blinded Evaluator assessment, the mean change from baseline in WSRS score was more than 1 grade for each side at all time points. For both Blinded Evaluator and subject assessments at 18 months, the mean improvement from baseline in WSRS score was more than 1 grade and was similar to the change from baseline observed at 2 weeks after re-treatment for each side. The mean change from baseline at all visits was statistically significant (p<0.001) for all follow-up Blinded Evaluator and subject assessments.

The mean volume injected (in mL) at each treatment is summarized in Table 5.12. The mean volume of Restylane injected into each nasolabial fold during the initial treatment was similar between sides. The 4½ month re-treatment side and the 9-month re-treatment side received virtually identical mean volume of RESTYLANE™ dermal filler, 1.1 mL at baseline and 0.5 mL at the touch-up visit. The mean volume injected at re-treatment (0.7 mL for re-treatment at either 4½ or 9 months) was less than at the initial treatment and was only slightly more than the amount required at the touch-up visit (0.5 mL for each re-treatment side). This shows that, even for subjects with a more extreme WSRS, the subjects required less product to achieve optimal correction at re-treatment.

TABLE 5.12

Volume (mL) of Restylane Treatment Used by Visit

| Visit | Side Assigned to Re-treatment at 4½ Months | Side Assigned to Re-treatment at 9 Months |
|---|---|---|
| Baseline | | |
| N | 75 | 75 |
| Mean ± SD | 1.1 ± 0.61 | 1.1 ± 0.56 |
| Median | 1.0 | 1.0 |
| Minimum | 0.1 | 0.2 |
| Maximum | 2.5 | 2.5 |
| Touch-up Visit | | |
| N | 44 | 44 |
| Mean ± SD | 0.5 ± 0.22 | 0.5 ± 0.21 |
| Median | 0.5 | 0.5 |
| Minimum | 0.2 | 0.2 |
| Maximum | 1.0 | 1.0 |
| Re-treatment Visit (4½ Months/9 months) | | |
| N | 67 | 63 |
| Mean ± SD | 0.7 ± 0.33 | 0.7 ± 0.36 |
| Median | 0.8 | 0.6 |
| Minimum | 0.2 | 0.1 |
| Maximum | 1.8 | 2.0 |

Note:
At visits where subjects were re-treated, grading was performed prior to re-treatment.

As can be seen from the above, even for the this more select population of individuals, the amount of the injectable filler composition used in the re-treatment session was only around 0.7 cc, compared to the 1.1 and 0.5 injections in the initial treatment session (per half of a subject's face).

Further discussion of various embodiments of a re-treatment method can be found in Narins, et al., "Persistence and Improvement of Nasolabial Fold Correction with Nonanimal-Stabilized Hyaluronic Acid 100,000 Gel Particles/mL Filler on Two Retreatment Schedules: Results up to 18 Months on Two Retreatment Schedules," *Dermatologic Surgery*, Volume 34 Issue Page S2-S8, June 2008, the entirety of which is incorporated herein by reference.

In this disclosure, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. The phrase "and/or" denotes a shorthand way of indicating that the specific combination is contemplated in combination and, separately, in the alternative.

The section headings used herein are for organizational purposes only and are not to be construed as limiting the described subject matter in any way.

It will be appreciated that there is an implied "about" prior to the amounts, concentrations, times, etc. discussed in the present teachings, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

The various devices and systems described above provide a number of ways to carry out the invention. It is to be understood that not necessarily all objectives or advantages described can be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method for providing an injectable filler composition to a subject for cosmetic purposes, said method comprising:
performing an initial treatment session on a subject, said initial treatment session comprising a first injection of a first injectable filler composition into the subject at a target area, thereby providing an increase in volume and/or firmness to the target area; and
performing a re-treatment session on the subject, said re-treatment session comprising a second injection of a second injectable filler composition into the target area at a time subsequent to the initial treatment session, wherein the second injection extends the increase in volume and/or firmness of the target area, wherein the time subsequent to the initial treatment session is in the range of 1 month to less than 9 months, and wherein the first and second injectable filler compositions comprises hyaluronic acid.

2. The method of claim 1, wherein the time subsequent to the initial treatment session is between 2 month and 9 months.

3. The method of claim 1, wherein the time subsequent to the initial treatment session is between 2 months and 6 months.

4. The method of claim 1, wherein the time subsequent to the initial treatment session is between 2 months and 5 months.

5. The method of claim 1, wherein the time subsequent to the initial treatment session is approximately 4.5 months.

6. The method of claim 1, wherein the time subsequent to the initial treatment session is 4.5 months.

7. The method of claim 1, wherein the initial treatment session results in a full correction of the target area.

8. The method of claim 1, wherein the initial treatment session comprises the first injection and a touch-up application within less than 1 month of the first injection.

9. The method of claim 8, wherein the initial injection comprises administering at least 1 cc of the injectable filler composition.

10. The method of claim 1, further comprising a touch-up application that comprises administering less than 1 cc of a third injectable filler composition.

11. The method of claim 1, wherein the re-treatment session comprises administering the second injectable filler composition in an amount that is approximately half of an amount of the first injectable filler composition used in the initial treatment session.

12. The method of claim 1, wherein the re-treatment session comprises administering no more than 80 percent of an amount of the first injectable filler composition used in the initial treatment session.

13. The method of claim 1, wherein the re-treatment session comprises administering no more than 60 percent of an amount of the first injectable filler composition used in the initial treatment session.

14. The method of claim 1, wherein the re-treatment session occurs between 2 months and 3 months after the initial treatment session.

15. The method of claim 1, wherein a substantial increase in baseline wrinkle severity is avoided between the initial treatment session and the re-treatment session.

16. The method of claim 1, wherein an improvement in a wrinkle severity rating score is maintained for at least 12 months after the re-treatment session.

17. The method of claim 1, wherein an improvement in a wrinkle severity rating scale is maintained for at least 13.5 months after the re-treatment session.

18. The method of claim 1, wherein an improvement of at least 1 in a wrinkle severity rating scale is maintained for at least 9 months after the re-treatment session.

19. The method of claim 1, wherein an improvement of a wrinkle severity rating scale is maintained for at least 10.5 months after the re-treatment session.

20. The method of claim 1, wherein no additional injection of any injectable filler composition is applied to the target area for at least 13.5 months following the re-treatment session.

21. The method of claim 1, wherein the subject receives no more than the first and second injections of any of the injectable filler composition for the target area for 18 months, and wherein the target area exhibits at least a one point improvement in its wrinkle severity rating scale (WSRS) at 13.5 months from the re-treatment session.

22. The method of claim 21, wherein the re-treatment session occurs no earlier than 3 months after the initial treatment session.

23. The method of claims 22, wherein the re-treatment session occurs no later than 6 months after the initial treatment session.

24. The method of claim 23, wherein the first injectable filler composition comprises hyaluronic acid and wherein the second injectable filler composition comprises hyaluronic acid.

25. The method of claim 1, wherein the re-treatment session comprises injecting an amount of the second injectable filler composition that is at least 30% of an amount of the first injectable filler composition that was used in the initial treatment session.

26. The method of claim 1, wherein the re-treatment session employs an amount of the second injectable filler composition that is at least 40% of an amount of the first injectable filler composition that was used in the initial treatment session.

27. The method of claim 1, wherein the re-treatment session is employed before a wrinkle improvement score drops below one point of improvement on a wrinkle severity rating scale.

28. The method of claim 1, wherein tissue expansile tension is maintained in the target area.

29. The method of claim 1, wherein the rate of absorption of the second injectable filler composition is slowed due to the initial treatment session.

30. The method of claim 1, wherein collagen production is stimulated in the target area.

31. The method of claim 1, wherein the target area is a location selected from the group consisting of an oral commissure, a marionette line, mandibular hollow, raise jowls, a frowning mouth, a pouty lower lip, a lateral expression line, a mental crease, a chin dimpling, a zygomatic hollow, a nasolabial fold, a tear trough, and a brow lift.

32. The method of claim 1, wherein the target area is touched-up after the first injection in the initial treatment session and prior to the re-treatment session.

33. The method of claim 1, wherein the first injectable filler composition further includes at least one substance selected from the group consisting of: collagen, bovine collagen, type I collagen, type II collagen, type III collagen, 3.5% bovine dermal collagen cross-linked by glutaraldehyde to form a latticework, natural human collagen, autologous collagen, polymethylmethacrylate microspheres, suspension of collagen fibers prepared from the patient's tissue, human tissue collagen matrix derived from cadaveric dermis, acellular human cadaveric dermis that has been freeze-dried, micronized acellular human cadaveric dermis that has been freeze-dried, cultured autologous fibroblasts, non-animal-stabilized hyaluronic acid derivative, microspheres of calcium hydroxyl appetite suspended in an aqueous gel carrier, dextran beads, dextran beads suspended in hylan gel of nonanimal origin, solubilized elastin peptides with bovine collagen, silicone, poly-L-lactic acid, polytetrafluoroethylene (PTFE), expanded polytetrafluoroethylene (e-PTFE), and any combination thereof.

34. The method of claim 1, wherein the extended increase continues for at least 9 months past the re-treatment session.

35. The method of claim 1, wherein the extended increase continues for at least 10 months past the re-treatment session.

36. The method of claim 1, wherein the extended increase continues for at least 12 months past the re-treatment session.

37. The method of claim 1, wherein the extended increase continues for at least 13 months past the re-treatment session.

38. The method of claim 1, wherein the extended increase comprises a larger mean improvement score 10.5 months after the re-treatment session than a mean improvement score 10.5 months after a single treatment session.

39. The method of claim 1, wherein a result of performing the method is to reduce a sign of aging in the subject.

40. A method for providing a target area of a subject with a continuing increase in firmness and/or volume following a re-treatment session of an injectable filler composition, said method comprising:
identifying a subject that will benefit from a continuing increase in a volume and/or firmness of a target area during a period following a re-treatment session and continuing for at least 13 months after the re-treatment session, wherein the volume and/or firmness increases throughout the period;
performing an initial treatment session on the subject, said initial treatment session comprising a first injection of a nonanimal stabilized hyaluronic acid, thereby providing an increase in volume and/or firmness to the target area; and
performing the re-treatment session on the subject, said re-treatment session comprising a second injection of the nonanimal stabilized hyaluronic acid into the target area at a time subsequent to the initial treatment session, wherein the subject's global aesthetic improvement scale continues to improve for at least 10.5 months following the re-treatment session, wherein the re-treatment session occurs 2 to 6 months after the initial treatment session, wherein the subject maintains at least a 1 point improvement in a global aesthetic improvement scale score and/or a wrinkle severity rating score for 18 months after the initial treatment session, and wherein the subject receives no additional injections of said nonanimal stabilized hyaluronic acid to the target area, except for the initial treatment session and the re-treatment session.

41. The method of claim 40, wherein identifying a subject comprises an identification of the subject as being moderate to extreme on a wrinkle rating severity scale.

42. The method of claim 33, wherein the first injectable filler composition further includes polymethylmethacrylate microspheres suspended in bovine collagen.

43. The method of claim 1, wherein the re-treatment session is performed when there is no apparent need to supply such an additional amount of an injectable filler to the subject.

44. The method of claim 40, wherein the re-treatment session is performed when there is no apparent need to supply such an additional amount of an injectable filler to the subject.

45. The method of claim 40, wherein the re-treatment session occurs 4.5 to 6 months after the initial treatment session.

46. The method of claim 1, wherein the re-treatment session occurs 4.5 to 9 months after the initial treatment session.

* * * * *